US010100128B2

(12) United States Patent
Eriksson

(10) Patent No.: US 10,100,128 B2
(45) Date of Patent: Oct. 16, 2018

(54) MONOCLONAL ANTI-TK1 ANTIBODIES

(71) Applicant: AROCELL AB, Uppsala (SE)

(72) Inventor: Staffan Eriksson, Lidingö (SE)

(73) Assignee: AROCELL AB, Uppsala (SE)

( * ) Notice: Subject to any disclaimer, the term of this patent is extended or adjusted under 35 U.S.C. 154(b) by 0 days.

(21) Appl. No.: 15/105,999

(22) PCT Filed: Dec. 18, 2014

(86) PCT No.: PCT/SE2014/051535
§ 371 (c)(1),
(2) Date: Jun. 17, 2016

(87) PCT Pub. No.: WO2015/094106
PCT Pub. Date: Jun. 25, 2015

(65) Prior Publication Data
US 2016/0311927 A1    Oct. 27, 2016

(30) Foreign Application Priority Data
Dec. 19, 2013    (SE) ...................................... 1351531

(51) Int. Cl.
*C07K 16/40* (2006.01)
*C12N 9/12* (2006.01)
*G01N 33/573* (2006.01)

(52) U.S. Cl.
CPC ............. *C07K 16/40* (2013.01); *C12N 9/1211* (2013.01); *C12Y 207/01021* (2013.01); *G01N 33/573* (2013.01); *C07K 2317/34* (2013.01); *G01N 2333/9122* (2013.01); *G01N 2800/26* (2013.01); *G01N 2800/54* (2013.01); *G01N 2800/7023* (2013.01)

(58) Field of Classification Search
CPC ............ C12Y 207/01021; C07K 16/40; C07K 2317/34
USPC ........................................ 424/133.1; 435/7.4
See application file for complete search history.

(56) References Cited

U.S. PATENT DOCUMENTS

| 6,083,707 A | 7/2000 | Eriksson et al. |
| 8,501,419 B2* | 8/2013 | Eriksson ............... C12N 9/1211 435/7.2 |
| 2010/0143244 A1 | 6/2010 | Lallatin |

FOREIGN PATENT DOCUMENTS

| CN | 1414017 A | 4/2003 |
| CN | 101275954 B | 10/2008 |
| CN | 102516390 A | 6/2012 |
| WO | 2004100760 A1 | 11/2004 |
| WO | 2008/142664 A2 | 11/2008 |

OTHER PUBLICATIONS

Eriksson et al. (Anticancer Research 28: 4009-4090 (2008); Abstracts of the 14th International Hamburg Symposium on Tumor Markers Dec. 7-9, 2008; Abstract #128).*
Gasparri et al. (European Journal of Cell Biology 88 (2009) 779-785).*
Jagarlamudi (PLoS ONE 10(9): e0137871. doi:10.1371/journal (Sep. 14, 2015); pp. 1-15).*
Karbownik et al. (Journal of Cellular Biochemistry 89:550-555 (2003)).*
Melissa M. Alegre et al., Serum Detection of Thymidine Kinase 1 as a Means of Early Detection of Lung Cancer, Anticancer Research, 34: 2145-2152 (2014).
Ruby Cooray et al., A New Assay Measuring Thymidine Kinase (TK1) Serum Concentrations—Comparison with the Diasorin TK-Liaison Activity Assay, Tumor Biol., 31 (Suppl 1):S67-S120 (2010).
Sharif Hanan et al., Quaternary structures of recombinant, cellular, and serum forms of Thymidine Kinase 1 from dogs and humans, BMC Biochemistry, 13:12, p. 1471-2091 (2012).
Thermo Scientific Pierce Antibody, Production and Purification Technical Handbook, Version 2, Thermo Fisher Scientific Inc., p. 1-41 (2010).
Chuanjing Wu et al., Production and characterisation of a novel chicken IgY antibody raised against C-terminal peptide from human thymidine kinase 1, Journal of Immunological Methods, 277:157-169 (2003).

* cited by examiner

*Primary Examiner* — Lynn A Bristol
(74) *Attorney, Agent, or Firm* — Porter, Wright Morris & Arthur LLP

(57) ABSTRACT

Monoclonal antibodies and fragments thereof are capable of binding to a serum form of human TK1. Kits and methods involve the use of such monoclonal antibodies or fragments.

14 Claims, 9 Drawing Sheets

Specification includes a Sequence Listing.

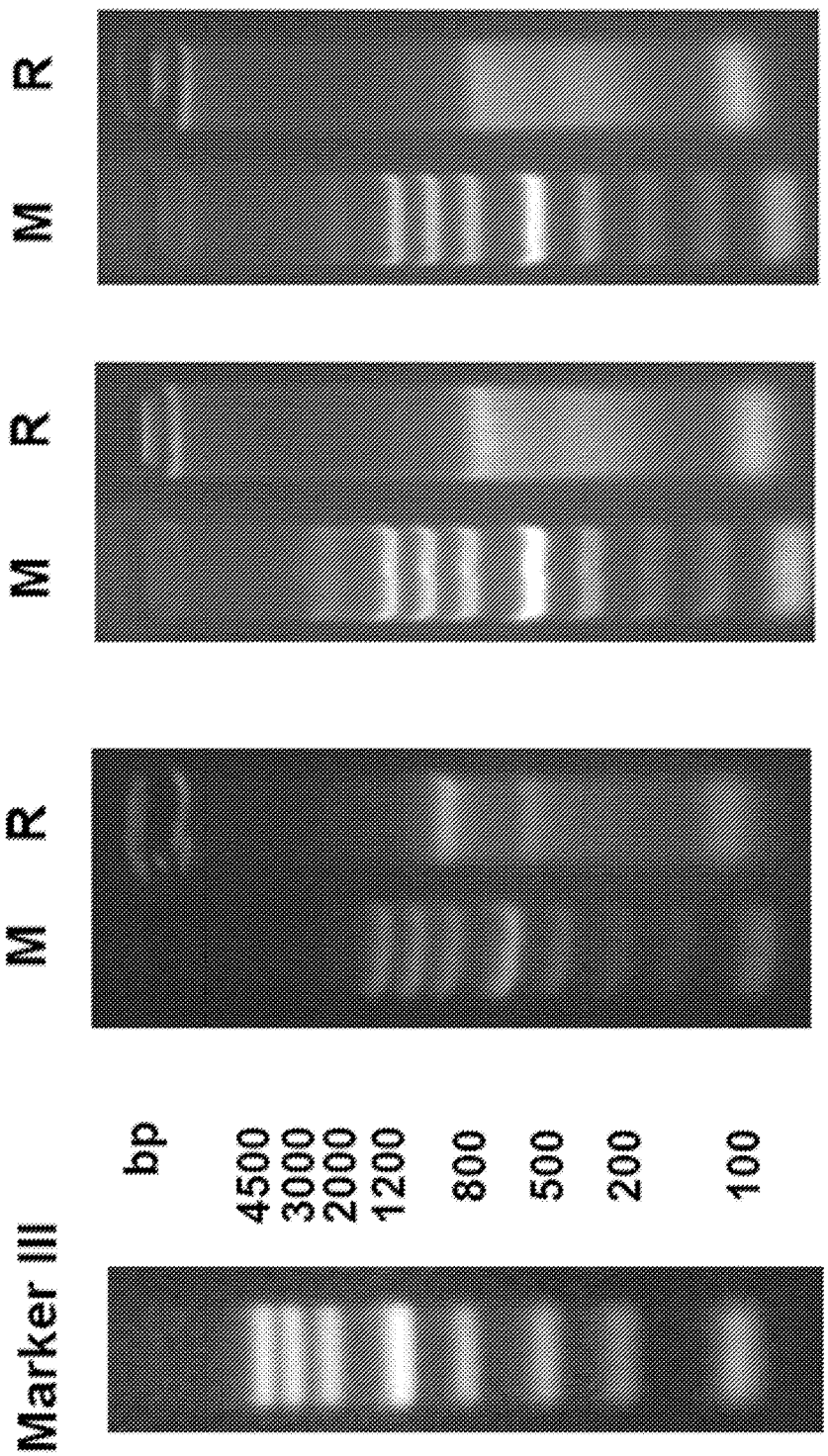

MONOCLONAL ANTI-TK1 ANTIBODIES

SEQUENCE LISTING

The Sequence Listing submitted herewith, entitled PCT_SE2014_051535_seq.txt, created Jun. 17, 2016, and having a size of 18,456 bytes, is incorporated herein by reference.

TECHNICAL FIELD

The present embodiments generally relate to monoclonal anti-TK1 antibodies, a kit and methods involving the use of such monoclonal anti-TK1 antibodies.

BACKGROUND

Thymidine kinase 1, TK1, (ATP: thymidine 5'-phosphotransferase, EC 2.7.1.21) is an enzyme involved in DNA precursor synthesis. A form of TK1 is present at high levels also in sera from humans and animals with malignant tumors. Therefore, serum TK1 activity measurements have been used for monitoring and for prognostic purpose in several different malignant diseases, but primarily in case of leukemia and lymphoma.

Furthermore, TK1 is the only proliferation marker that can be determined in the blood and it is likely to provide a large clinical benefit if available as a routine laboratory test [1-8].

The serum TK1 activity has been measured using a radioactive substrate $^{125}$I-dUrd (the PROLIFIGEN® TK-REA, DiaSorin Inc) for several decades, but this radioenzymatic assay has had limited use and only in case of malignant hematologic malignancies [1, 2, 6]. A non-radiometric TK1 activity assay (TK LIAISON® assay, DiaSorin Inc.) has been available in recent years. This is a sensitive and robust assay and has provided clinically valuable information in humans and dogs with hematologic malignancies, particularly for monitoring therapy and predicting relapse [8, 9].

During the last 15 years antibodies against human TK1 have been available and enabled the determination of TK1 protein levels, in contrast to TK1 activity, in different hematologic and solid tumors, such as breast carcinomas [5, 10, 11], and several other forms of solid and hematologic tumors [11, 12].

The TK1 protein determinations rely mainly on a dot blot procedure based on anti-TK1 antibodies produced against the C-terminal part of TK1 [3, 5, 10-13]. The main reason for choosing this strategy for antibody production is that the C-terminal region is involved in the cell cycle regulation of TK1 [14-16]. It contains a recognition sequence for initiating the degradation of TK1 during mitosis and it has been assumed that this is an exposed region to which it could be possible to generate antibodies [3, 8, 13, 20, 23-25]. Although the dot blot assay has been used successfully in a number of studies [5, 10-13] the major limitation is that it is not a routine method in clinical laboratory practice. There are now more than six different anti-TK1 antibody preparations available commercially and several have been shown to react with recombinant and cellular TK1 (www.acris-antibodies.com). However, there is at present no antibody based assay for serum TK1 in routine clinical practice.

The main reason for the difficulty in establishing a sensitive and robust assay for serum TK1 is most likely related to the complex and variable forms of TK1 present in blood. Recently, several studies, both with the human and dog TK1 enzymes, have been conducted characterizing the recombinant, cellular and serum forms of TK1 [17]. It was found that TK1 exists in multiple oligomeric complexes and importantly only a sub-fraction of these complexes were enzymatically active. This is particularly the case for serum TK1 in patients with solid tumor diseases. The oligomerization seems to be related to the formation of disulfide cross linking occurring in the blood, but most likely also when the tumor cells disintegrate and TK1 is transported into the blood stream. Treatment with reducing agents leads to some reorganization of the serum TK1 complexes [2, 17], but the consequences of these facts for immune assay design have not so far been addressed. The fact that a major part of the TK1 protein in blood is enzymatically inactive may explain that TK1 enzyme activity measurements are not very effective in case of solid tumor diseases [18]. Thus, there is a large need to establish routine in vitro diagnostic procedures that can measure serum TK1 with sufficient sensitivity for clinical use.

SUMMARY

It is an objective to provide a monoclonal antibody or fragment capable of binding to a serum form of human TK1.

This and other objectives are met by embodiments as disclosed herein.

An aspect of the embodiments relates to a monoclonal antibody or a fragment of a monoclonal antibody capable of binding to a serum form of human thymidine kinase 1 (TK1). The monoclonal antibody or fragment has specificity for an epitope selected from a group consisting of:
  GEAVAARKLF (SEQ ID NO: 2) of human TK1;
  at least one or NCPVPGKPGE (SEQ ID NO: 4), PVPG-KPGEAV (SEQ ID NO: 5) and NCPVPGKPGEAV (SEQ ID NO: 3) of human TK1; and
  a conformation dependent epitope of human TK1.

Another aspect of the embodiments relates to a method for determining a level of cellular and/or serum TK1 material in a body sample. The method comprises contacting the body sample with a monoclonal antibody or fragment according to above. The method also comprises detecting an amount of bound monoclonal antibody or fragment.

A further aspect of the embodiments relates to kit for determining a level of cellular and/or serum TK1 material in a body sample. The kit comprises a first monoclonal antibody according to above immobilized to a solid support or intended to be immobilized to the solid support. The kit also comprises a second monoclonal antibody according to above. In this aspect, the first monoclonal antibody has specificity for a first epitope selected from a group consisting of:
  GEAVAARKLF (SEQ ID NO: 2) of human TK1,
  at least one of NCPVPGKPGE (SEQ ID NO: 4), PVPG-KPGEAV (SEQ ID NO: 5) and NCPVPGKPGEAV (SEQ ID NO: 3) of human TK1, and
  a conformation dependent epitope of human TK1. The second monoclonal antibody has specificity for a second, different epitope selected from this group.

Yet another aspect of the embodiments relates to a method for estimating the likelihood of recurrence of a tumor in a subject. The method comprises determining a level of serum TK1 material in a body sample from the subject using a method or a kit according to above. The method also comprises comparing the level of serum TK1 material in the body sample with a level of serum TK1 material representative of a population of healthy subjects or with a level of serum TK1 material previously determined in the subject.

A further aspect of the embodiments relates to a method for determining cell proliferation in a subject. The method comprises determining a level of serum TK1 material in a body sample from the subject using a method or a kit according to above. The method also comprises determining the cell proliferation based on the level of serum TK1 material in the body sample.

Yet another aspect of the embodiments relates to a method for determining a proliferation process response in a subject suffering from a malignant disease. The method comprises determining a level of serum TK1 material in a body sample from the subject using a method or a kit according to above. The method also comprises determining the proliferation process response based on the level of serum TK1 material in the body sample.

A further aspect of the embodiments relates to a method for determining a level of inflammation, infection, or tumor cell proliferation in a subject. The method comprises determining a level of serum TK1 material in a body sample from the subject using a method or a kit according to above. The method also comprises determining the level of inflammation, infection or tumor cell proliferation based on the level of serum TK1 material in the body sample.

Still another aspect of the embodiments relates to an isolated peptide consisting of the amino acid sequence GEAVAARKLF (SEQ ID NO: 2), NCPVPGKPGE (SEQ ID NO: 4), PVPGKPGEAV (SEQ ID NO: 5, or NCPVPGK-PGEAV (SEQ ID NO: 3).

Yet another aspect of the embodiments relates to a method of producing a monoclonal antibody capable of binding to a serum form of human TK1. The method comprises immunizing a non-human animal with a first peptide conjugate comprising a peptide having amino acid sequence GQPAG-PDNKENCPVPGKPGEAVAARKLFAPQ (SEQ ID NO: 1) coupled to a first carrier protein or a second peptide conjugate comprising the peptide having amino acid sequence GQPAGPDNKENCPVPGKPGEAVAARKLFAPQ (SEQ ID NO: 1) coupled to a second carrier protein that is different from the first carrier protein. The method also comprises isolating splenocytes from the non-human animal with blood titers for the first peptide conjugate or the second peptide conjugate. The method further comprises forming hybridomas by fusing the splenocytes with myelomas. The method additionally comprises screening supernatant from hydridomas, resulting from immunization with the first peptide conjugate, for titers for the second peptide conjugate and screening supernatant from hydridomas, resulting from immunization with the second peptide conjugate, for titers for the first peptide conjugate. The method further comprises selecting a hybridoma producing a monoclonal antibody capable of binding to the first peptide conjugate, to the second peptide conjugate and to human rTK1. The method additionally comprises isolating the monoclonal antibody from supernatant of the selected hybridoma.

The monoclonal antibodies and fragments of the embodiments have excellent properties in terms of being able to bind to the serum form of human TK1 and can therefore be used in various kits and methods involving determining the level of the serum form of human TK1 in a sample.

BRIEF DESCRIPTION OF THE DRAWINGS

The embodiments, together with further objects and advantages thereof, may best be understood by making reference to the following description taken together with the accompanying drawings, in which:

FIGS. 6A-6D illustrate agarose gel electrophoresis of total RNA of XPA 210-Ar1 (FIG. 6B), XPA 210-Ar2 (FIG. 6C) and XPA 210-Ar3 (FIG. 6D) producing hybridoma cells. FIG. 6A illustrates the DNA marker Marker III, which is also present in lane M of FIGS. 6B-6D, where lane R indicates total RNA from the respective hybridoma cells.

DETAILED DESCRIPTION

Figure 1:
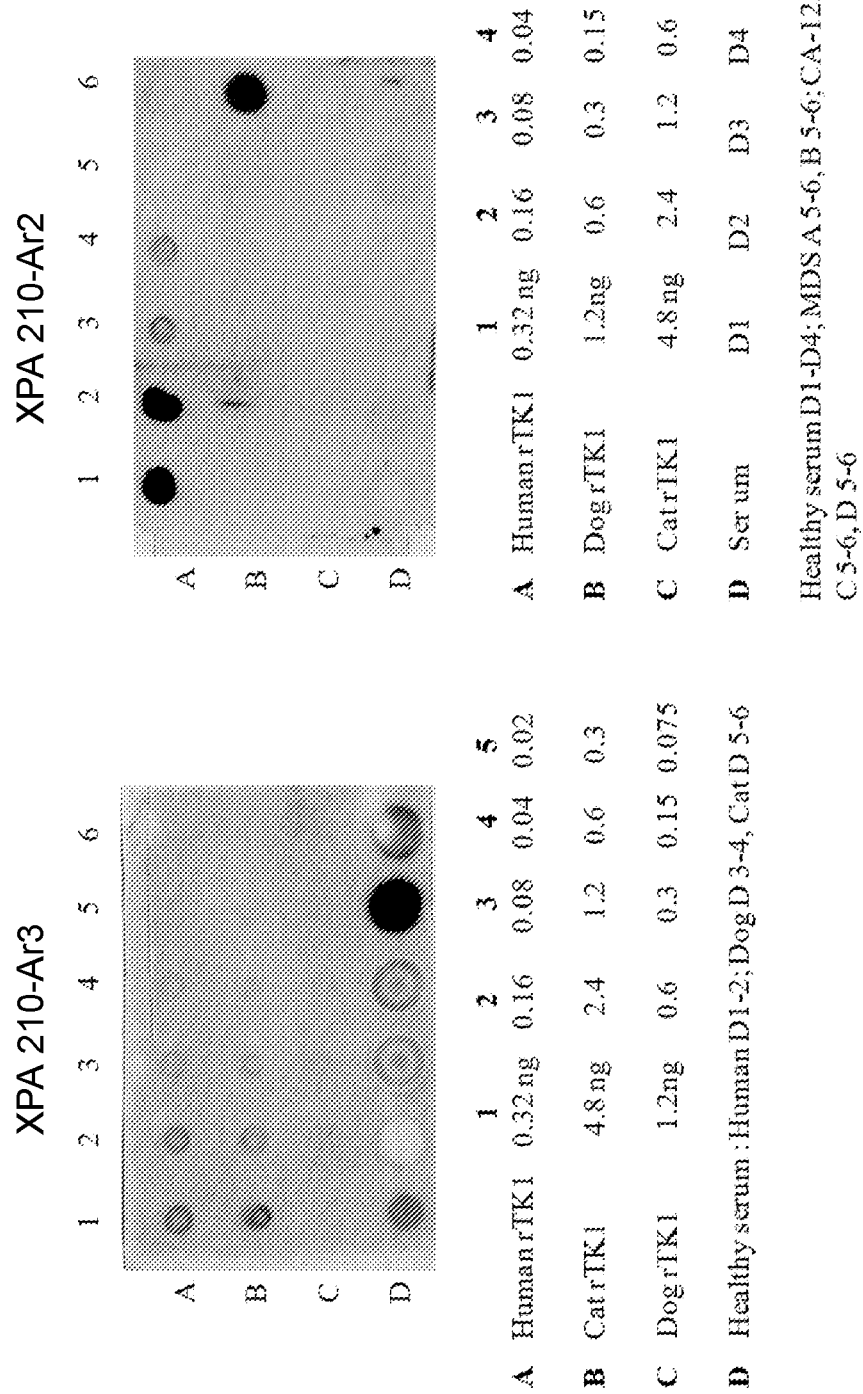
FIG. 1 illustrates the results of dot blot assays with supernatants from anti-XPA 210 peptide hybridomas and recombinant TK1 preparations and sera from healthy and cancer patients. Myelodysplastic syndrome (MDS) is a diverse collection of hematological medical conditions that involve ineffective production of the myeloid class of blood cells and is also known as preleukemia. CA-125 indicates in this case patients suspected of suffering from ovarian cancer.

The present embodiments generally relate to monoclonal anti-thymidine kinase 1 (anti-TK1) antibodies or antibody fragments and to methods and kits involving the use of such monoclonal anti-TK1 antibodies or antibody fragments.

The monoclonal anti-TK1 antibodies and fragments of the embodiments are highly useful as diagnostic and clinical tools since these monoclonal anti-TK1 antibodies and fragments are capable of binding to a serum form of human TK1.

There are monoclonal anti-TK1 antibodies known in the art. Although these antibodies are capable of binding to human recombinant TK1 (rTK1) and, in varying degrees, to a cellular form of human TK1, sometimes denoted as cytosolic TK1, they are not efficient in terms of being able to bind to the serum form of human TK1 in body samples, such as in serum or blood samples.

TK1 in humans are present in various forms depending on the presence of certain molecules, e.g. presence or absence of adenosine triphosphate (ATP); depending on the concentration of the protein, i.e. high or low concentration; depending on the type of the protein, i.e. native or recombinant TK1; and depending on the site of the protein, i.e. in serum or cytoplasma.

Generally, cytosolic and recombinant human TK1 occurs as tetramers in the presence of ATP or at high concentration, and as dimers in the absence of ATP or at low concentration. The tetramer form of cytosolic and recombinant human TK1 has high TK1 activity whereas the dimer form has lower TK1 activity [26].

Human serum TK1, in clear contrast, can be in the form of high molecular weight complexes, such as oligomers or comprising such oligomers, having serum TK1 activity and dimer and tetramer forms having very low or even lacking serum TK1 activity.

Commercially available anti-TK1 antibodies (3B3.E11 from Abcam; M02, clone F12 from Abnova; EPR3194 and EPR3193, rabbit monoclonal antibodies from Abnova) do not react sufficiently well with serum TK1. These anti-TK1 antibodies are generated based on human recombinant TK1. This indicates, together with experimental results as presented herein, that the generation of monoclonal anti-TK1 antibodies based on human recombinant TK1 is generally inefficient and will typically not produce anti-TK1 antibodies capable of binding to the serum form of TK1 at sufficient binding strength.

Furthermore, monoclonal anti-TK1 antibodies raised against the same portion of the TK1 protein will have very different specificity and binding properties with regard to the serum form of TK1 as shown herein. This means that a monoclonal anti-TK1 antibody recognizing a first epitope in a portion of the TK1 protein may bind to the serum form of human TK1 whereas another monoclonal anti-TK1 antibody recognizing a second, different epitope in the same portion of the TK1 protein will not bind well to the serum form of TK1 even if both monoclonal anti-TK1 antibodies have been raised against the same general portion of the TK1 protein.

A tentative explanation of this variation in binding properties of different monoclonal anti-TK1 antibodies is most likely that it is only monoclonal anti-TK1 antibodies that have specificity for special epitopes in human TK1 that are efficient in having capability of binding to the serum form of human TK1. The present embodiments have identified such special epitopes that enable formation of monoclonal anti-TK1 antibodies and antibody fragments with the desired property of being able to bind to the serum form of human TK1.

The unique nature of the monoclonal anti-TK1 antibodies described herein is therefore most likely, at least in part, due to their epitope binding properties.

Accordingly, an aspect of the embodiments relates to a monoclonal antibody or a fragment of a monoclonal antibody capable of binding to a serum form of human TK1. The monoclonal antibody or fragment has specificity for en epitope selected from a group consisting of:
  GEAVAARKLF (SEQ ID NO: 2) of human TK1;
  at least one of NCPVPGKPGE (SEQ ID NO: 4), PVPG-KPGEAV (SEQ ID NO: 5) and NCPVPGKPGEAV (SEQ ID NO: 3) of human TK1; and
  a conformation dependent epitope of human TK1.

Experimental data as presented herein indicates that the epitopes of the above presented group are key epitopes in human TK1 with regard to producing a monoclonal anti-TK1 antibody or fragment capable of binding to the serum form of human TK1.

The epitope GEAVAARKLF (SEQ ID NO: 2) corresponds to amino acids number 213 to 222 in human TK1. This epitope is generally denoted 10-mer or 10-mer peptide herein.

The second epitope of the above presented group in turn comprises three related sequences present in the portion of human TK1 extending from amino acid number 205 to 216. These related sequences are NCPVPGKPGE (SEQ ID NO: 4) generally denoted peptide 7 herein, PVPGKPGEAV (SEQ ID NO: 5) generally denoted peptide 8 herein, and NCPVPGKPGEAV (SEQ ID NO: 3) generally denoted 12-mer or 12-mer peptide herein.

These epitopes (SEQ ID NO: 2-5) are present in the C-terminal region of human TK1. This C-terminal region of TK1 is involved in the cell cycle regulation of TK1 and contains a recognition sequence for initiating the degradation of TK1 during mitosis.

These epitopes are also part of a longer sequence GQPAGPDNKENCPVPGKPGEAVAARKLFAPQ (SEQ ID NO: 1) in the C-terminal part of human TK1. This longer sequence is generally denoted XPA 210, 31-mer or 31-mer peptide herein.

The third epitope of the above presented group is a conformation dependent epitope of human TK1. This means that a monoclonal anti-TK1 antibody or fragment having specificity for the conformation dependent epitope does not show any distinct binding to any single short, i.e. 10-12 amino acid long, peptide portion of human TK1. In clear contrast, the binding of the monoclonal anti-TK1 antibody or fragment will in this case be conformation dependent with an epitope or antigenic domain consisting of multiple, i.e. at least two, regions that are not adjacent each other in the primary sequence of human TK1 but formed by a certain three dimensional (3D) conformation of an antigenic domain. Thus, in the 3D structure of human TK1 these multiple regions will be present adjacent or close to each other to together constitute or form the conformation dependent epitope.

In a preferred embodiment, the conformation dependent epitope is a conformation dependent epitope present in the C-terminal part of human TK1. In a further preferred embodiment, the conformation dependent epitope is a conformation dependent epitope present in the C-terminal part of human TK1 extending from amino acid number 195 to amino acid number 225, i.e. the part of human TK1 corresponding to XPA 210.

Thus, folding of the primary amino acid sequence of human TK1 to form a 3D protein structure brings multiple regions in the C-terminal and preferably in the part of the C-terminal corresponding to XPA 210 close together to enable formation of the conformation dependent epitope even if these regions are not adjacent each other in the primary sequence of human TK1.

In a preferred embodiment, the monoclonal antibody or fragment of the embodiments is capable of binding not only to the serum form of human TK1 but also to human recombinant TK1 (rTK1)

In a preferred embodiment, the monoclonal antibody or fragment of the embodiments is capable of binding not only to the serum form of human TK1 but also to a cellular form of human TK1, i.e. cytosolic TK1.

In a preferred embodiment, the monoclonal antibody or fragment of the embodiments is capable of binding not only to the serum form of human TK1 but also to human rTK1 and the cellular form of human TK1.

Hence, the monoclonal antibodies and fragments of the embodiments have very versatile use since they are able to bind to different forms of TK1, i.e. preferably serum and cellular forms of human TK1 and human rTK1. These binding properties of the monoclonal antibodies and fragments are believed to be due to the identification of the selected epitopes, to which the monoclonal antibodies and fragments have specificity. Other monoclonal anti-TK1 antibodies binding to the C-terminal part of human TK1 may be able to bind to human rTK1 and/or cellular forms of human TK1 but do not bind well to serum forms of human TK1. This is a unique property of the present monoclonal antibodies and fragments.

The monoclonal antibody or fragment is preferably also capable of binding to a peptide having amino acid sequence GQPAGPDNKENCPVPGKPGEAVAARKLFAPQ (SEQ ID NO: 1), i.e. XPA 210.

The monoclonal antibody or fragment of the embodiments is preferably obtainable by a process, such as obtained by the process, involving the following steps.

Immunizing a non-human animal with a first peptide conjugate comprising a peptide having amino acid sequence GQPAGPDNKENCPVPGKPGEAVAARKLFAPQ (SEQ ID NO: 1) coupled to a first carrier protein, preferably bovine serum albumin (BSA), or a second peptide conjugate comprising the peptide having amino acid sequence GQPAGPDNKENCPVPGKPGEAVAARKLFAPQ (SEQ ID NO: 1) coupled to a second carrier protein that is different from the first carrier protein, preferably keyhole limpet cyanine (KLH).

The non-human animal can be selected from various animals traditionally used for antibody production including, but not limited to, mice, rats, chickens, goats, sheep, guinea pigs, hamsters, rabbits and horses. In a particular embodiment, the non-human animal is a non-human mammal.

Splenocytes are isolated from the non-human animal with blood titers (antibody titer) for the first peptide conjugate or the second peptide conjugate.

Generally, multiple non-human animals are immunized with the first peptide conjugate or the second conjugate. In such a case, those non-human animals that show high blood titers for the first peptide conjugate or the second peptide conjugate are identified. Splenocytes are then isolated from these identified non-human animals.

A non-human animal showing blood titer implies that the blood or serum of the non-human animal comprises antibodies that bind to the first peptide conjugate or the second peptide conjugate and more preferably bind to the peptide GQPAGPDNKENCPVPGKPGEAVAARKLFAPQ (SEQ ID NO: 1) of the first and second peptide conjugates.

Hybridomas are then formed by fusing the isolated splenocytes with myelomas according to techniques well known in the art.

The supernatant from the hydridomas, resulting from immunization with the first peptide conjugate, are screened for titers for the second peptide conjugate (antibody titer). Correspondingly, the supernatant from the hybridomas, resulting from immunization with the second peptide conjugate, are screened for titers for the first peptide conjugate (antibody titer).

This screening is performed to avoid antibodies produced against the carrier proteins, such as BSA or KLH, used in the respective immunizations.

Thereafter one or more hybridomas producing monoclonal antibodies capable of binding to the first peptide conjugate and to the second peptide conjugate is or are selected. In a particular embodiment, at least one hybridoma producing monoclonal antibodies capable of binding to the first peptide conjugate, to the second peptide conjugate and to human rTK1 is selected.

A monoclonal antibody of the embodiments is then isolated from the supernatant of the selected hybridoma.

In an embodiment, the monoclonal antibody or fragment has complementarity determining regions (CDRs) having amino acid sequences from a group consisting of:

DYEMH (SEQ ID NO: 6), or an amino acid sequence having at least 90% and preferably at least 95% sequence identity to SEQ ID NO: 6;

AIHPGYGGTAYNQKFKG (SEQ ID NO: 7), or an amino acid sequence having at least 90% and preferably at least 95% sequence identity to SEQ ID NO: 7;

FITKFDY (SEQ ID NO: 8), or an amino acid sequence having at least 90% and preferably at least 95% sequence identity to SEQ ID NO: 8;

KSSQSLLDSDGKTFLN (SEQ ID NO: 9), or an amino acid sequence having at least 90% and preferably at least 95% sequence identity to SEQ ID NO: 9;

LVSKLDS (SEQ ID NO: 10), or an amino acid sequence having at least 90% and preferably at least 95% sequence identity to SEQ ID NO: 10; and WQGTHFPWT (SEQ ID NO: 11), or an amino acid sequence having at least 90% and preferably at least 95% sequence identity to SEQ ID NO: 11.

In a particular embodiment, the monoclonal antibody or fragment has CDRs having amino acid sequences selected from a group consisting of SEQ ID NO: 6, SEQ ID NO: 7, SEQ ID NO: 8, SEQ ID NO: 9, SEQ ID NO: 10 and SEQ ID NO: 11.

In a particular embodiment, the monoclonal antibody or fragment has a variable heavy (VH) CDR1 having amino acid sequence SEQ ID NO: 6, or an amino acid sequence having at least 90% and preferably at least 95% sequence identity to SEQ ID NO: 6; a VH CDR2 having amino acid sequence SEQ ID NO: 7, or an amino acid sequence having at least 90% and preferably at least 95% sequence identity to SEQ ID NO: 7; and a VH CDR3 having amino acid sequence SEQ ID NO: 8, or an amino acid sequence having at least 90% and preferably at least 95% sequence identity to SEQ ID NO: 8. The monoclonal antibody or fragment preferably also or alternatively has a variable light (VL) CDR1 having amino acid sequence SEQ ID NO: 9, or an amino acid sequence having at least 90% and preferably at least 95% sequence identity to SEQ ID NO: 9; a VL CDR2 having amino acid sequence SEQ ID NO: 10, or an amino acid sequence having at least 90% and preferably at least 95% sequence identity to SEQ ID NO: 10; and a VL CDR3 having amino acid sequence SEQ ID NO: 11, or an amino acid sequence having at least 90% and preferably at least 95% sequence identity to SEQ ID NO: 11.

In a particular embodiment, the monoclonal antibody or fragment has a VH CDR1 having amino acid sequence SEQ ID NO: 6; a VH CDR2 having amino acid sequence SEQ ID NO: 7; a VH CDR3 having amino acid sequence SEQ ID NO: 8; a VL CDR1 having amino acid sequence SEQ ID NO: 9; a VL CDR2 having amino acid sequence SEQ ID NO: 10; and a VL CDR3 having amino acid sequence SEQ ID NO: 11.

A monoclonal antibody according to this particular embodiment is denoted XPA 210-Ar1 herein.

In another embodiment, the monoclonal antibody or fragment has CDRs having amino acid sequences from a group consisting of:

DYEMH (SEQ ID NO: 6), or an amino acid sequence having at least 90% and preferably at least 95% sequence identity to SEQ ID NO: 6;

AILPGSGGTAYNQKFKG (SEQ ID NO: 12), or an amino acid sequence having at least 90% and preferably at least 95% sequence identity to SEQ ID NO: 12;

LITTFDY (SEQ ID NO: 13), or an amino acid sequence having at least 90% and preferably at least 95% sequence identity to SEQ ID NO: 13;

KSSQSLLDSDGKTYLN (SEQ ID NO: 14), or an amino acid sequence having at least 90% and preferably at least 95% sequence identity to SEQ ID NO: 14;

LVSKLDS (SEQ ID NO: 10), or an amino acid sequence having at least 90% and preferably at least 95% sequence identity to SEQ ID NO: 10; and WQGTHFPWT (SEQ ID NO: 11), or an amino acid sequence having at least 90% and preferably at least 95% sequence identity to SEQ ID NO: 11.

In a particular embodiment, the monoclonal antibody or fragment has CDRs having amino acid sequences selected from a group consisting of SEQ ID NO: 6, SEQ ID NO: 12, SEQ ID NO: 13, SEQ ID NO: 14, SEQ ID NO: 10 and SEQ ID NO: 11.

In a particular embodiment, the monoclonal antibody or fragment has a VH CDR1 having amino acid sequence SEQ ID NO: 6, or an amino acid sequence having at least 90% and preferably at least 95% sequence identity to SEQ ID NO: 6; a VH CDR2 having amino acid sequence SEQ ID NO: 12, or an amino acid sequence having at least 90% and preferably at least 95% sequence identity to SEQ ID NO: 12; and a VH CDR3 having amino acid sequence SEQ ID NO: 13, or an amino acid sequence having at least 90% and preferably at least 95% sequence identity to SEQ ID NO: 13. The monoclonal antibody or fragment preferably also or alternatively has a VL CDR1 having amino acid sequence SEQ ID NO: 14, or an amino acid sequence having at least 90% and preferably at least 95% sequence identity to SEQ ID NO: 14; a VL CDR2 having amino acid sequence SEQ ID NO: 10, or an amino acid sequence having at least 90% and preferably at least 95% sequence identity to SEQ ID NO: 10; and a VL CDR3 having amino acid sequence SEQ ID NO: 11, or an amino acid sequence having at least 90% and preferably at least 95% sequence identity to SEQ ID NO: 11.

In a particular embodiment, the monoclonal antibody or fragment has a VH CDR1 having amino acid sequence SEQ ID NO: 6; a VH CDR2 having amino acid sequence SEQ ID NO: 12; a VH CDR3 having amino acid sequence SEQ ID NO: 13; a VL CDR1 having amino acid sequence SEQ ID NO: 14; a VL CDR2 having amino acid sequence SEQ ID NO: 10; and a VL CDR3 having amino acid sequence SEQ ID NO: 11.

A monoclonal antibody according to this particular embodiment is denoted XPA 210-Ar2 herein.

In a further embodiment, the monoclonal antibody or fragment has CDRs having amino acid sequences from a group consisting of:

SGYSWH (SEQ ID NO: 15), or an amino acid sequence having at least 90% and preferably at least 95% sequence identity to SEQ ID NO: 15;

YIHYSGSTTYNPSLKG (SEQ ID NO: 16), or an amino acid sequence having at least 90% and preferably at least 95% sequence identity to SEQ ID NO: 16;

WGTGHWYFDV (SEQ ID NO: 17), or an amino acid sequence having at least 90% and preferably at least 95% sequence identity to SEQ ID NO: 17;

RSSTGAVTTTNYAN (SEQ ID NO: 18), or an amino acid sequence having at least 90% and preferably at least 95% sequence identity to SEQ ID NO: 18;

GTNNRVP (SEQ ID NO: 19), or an amino acid sequence having at least 90% and preferably at least 95% sequence identity to SEQ ID NO: 19; and ALWYSNHWV (SEQ ID NO: 20), or an amino acid sequence having at least 90% and preferably at least 95% sequence identity to SEQ ID NO: 20.

In a particular embodiment, the monoclonal antibody or fragment has CDRs having amino acid sequences selected from a group consisting of SEQ ID NO: 15, SEQ ID NO: 16, SEQ ID NO: 17, SEQ ID NO: 18, SEQ ID NO: 19 and SEQ ID NO: 20.

In a particular embodiment, the monoclonal antibody or fragment has a VH CDR1 having amino acid sequence SEQ ID NO: 15, or an amino acid sequence having at least 90% and preferably at least 95% sequence identity to SEQ ID NO: 15; a VH CDR2 having amino acid sequence SEQ ID NO: 16, or an amino acid sequence having at least 90% and preferably at least 95% sequence identity to SEQ ID NO: 16; and a VH CDR3 having amino acid sequence SEQ ID NO: 17, or an amino acid sequence having at least 90% and preferably at least 95% sequence identity to SEQ ID NO: 17. The monoclonal antibody or fragment preferably also or alternatively has a VL CDR1 having amino acid sequence SEQ ID NO: 18, or an amino acid sequence having at least 90% and preferably at least 95% sequence identity to SEQ ID NO: 18; a VL CDR2 having amino acid sequence SEQ ID NO: 19, or an amino acid sequence having at least 90% and preferably at least 95% sequence identity to SEQ ID NO: 19; and a VL CDR3 having amino acid sequence SEQ ID NO: 20, or an amino acid sequence having at least 90% and preferably at least 95% sequence identity to SEQ ID NO: 20.

In a particular embodiment, the monoclonal antibody or fragment has a VH CDR1 having amino acid sequence SEQ ID NO: 15; a VH CDR2 having amino acid sequence SEQ ID NO: 16; a VH CDR3 having amino acid sequence SEQ ID NO: 17; a VL CDR1 having amino acid sequence SEQ ID NO: 18; a VL CDR2 having amino acid sequence SEQ ID NO: 19; and a VL CDR3 having amino acid sequence SEQ ID NO: 20.

A monoclonal antibody according to this particular embodiment is denoted XPA 210-Ar3 herein.

The fragment of the monoclonal antibody of the embodiments can be any fragment of a monoclonal antibody capable of binding to the serum form of human TK1 and can be selected from a group consisting of a single chain antibody, a Fv fragment, a scFv fragment, a Fab fragment, a F(ab')2 fragment, a Fab' fragment, a Fd fragment, a single-domain antibody (sdAb), a scFv-Fc fragment, a di-scFv fragment and a CDR region.

The monoclonal antibody or fragment of the embodiments is preferably an isolated monoclonal antibody or fragment, such as isolated from the supernatant of the previously described hybridoma.

The monoclonal antibody can be a humanized monoclonal antibody or a chimeric monoclonal antibody capable of binding to the serum form of human TK1.

The specificity of a monoclonal antibody can be determined based on affinity and/or avidity. The affinity, represented by the equilibrium constant for the dissociation of an antigen with the monoclonal antibody ($K_d$), is a measure for the binding strength between an antigenic determinant and an antigen-binding site on the monoclonal antibody. The lesser the value of $K_d$, the stronger the binding strength between the antigenic determinant and the monoclonal antibody. Alternatively, the affinity can also be expressed as the affinity constant ($K_a$), which is $1/K_d$. As will be clear to the skilled person, affinity can be determined in a manner known per se, depending on the specific antigen of interest.

Avidity is the measure of the strength of binding between a monoclonal antibody and the pertinent antigen. Avidity is related to both the affinity between an antigenic determinant and its antigen binding site on the monoclonal antibody and the number of pertinent binding sites present on the monoclonal antibody.

Typically, monoclonal antibodies will bind to their antigen with a dissociation constant ($K_d$) of $10^{-5}$ to $10^{-12}$ moles/liter (M) or less, and preferably $10^{-7}$ to $10^{-12}$ M or less and more preferably $10^{-8}$ to $10^{-12}$ M, i.e. with an association constant ($K_a$) of $10^5$ to $10^{12}$ $M^{-1}$ or more, and preferably $10^7$ to $10^{12}$ $M^{-1}$ or more and more preferably $10^8$ to $10^{12}$ $M^{-1}$.

Generally, any $K_d$ value greater than $10^{-4}$ M (or any $K_a$ value lower than $10^4 M^{-1}$) is generally considered to indicate non-specific binding.

Preferably, a monoclonal antibody or fragment of the embodiments will bind to the serum form and/or recombinant form of human TK1 with an affinity less than 500 nM, preferably less than 200 nM, more preferably less than 10 nM, such as less than 5 nM. Preliminary binding studies as presented herein indicate that monoclonal antibodies of the embodiments has affinity corresponding to KD values lower than 5 nM and for some even lower than 1 nM with regard to binding to recombinant human TK1.

Specific binding of a monoclonal antibody to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art.

Another aspect of the embodiments relates to a method for determining a level of cellular and/or serum TK1 material in a body sample. The method comprises contacting the body sample with a monoclonal antibody or a fragment according to the embodiments. The method also comprises detecting an amount of bound monoclonal antibody or fragment.

Any prior art techniques to detect the amount of bound monoclonal antibody or fragment can be used in the present method. For instance, the detection can be direct or indicted, and may generate a fluorescent or chromogenic signal. Direct detection typically involves the use of a monoclonal antibody or fragment that is conjugated to a label. Indirect detection utilizes a labeled secondary antibody raised against the host species of the monoclonal antibody or fragment.

Commonly used labels for visualization of binding of antibody to epitope includes fluorophores and enzymes that convert soluble substrates into chromogenic end products.

The body sample is preferably selected from a group consisting of a cell sample, a tissue sample, a blood sample, a serum sample, a cerebrospinal fluid sample, a peural fluid sample, a synovial fluid sample and a peritoneal cavity fluid sample. In a preferred embodiment, the body sample is a body fluid sample and preferably selected from a group consisting of a blood sample, a serum sample, a cerebrospinal fluid sample, a peural fluid sample, a synovial fluid sample and a peritoneal cavity fluid sample. In a particular embodiment, the body (fluid) sample is a blood sample or a serum sample.

Thus, the monoclonal antibodies and fragments of the embodiments can be used to determine a level, i.e. an amount, of cellular and/or serum TK1 material in a body sample. The monoclonal antibodies and fragments of the embodiments are believed to be able to bind to and thereby enable determination of the level of cellular or serum TK1 in its various forms, such as dimers, tetramers, and oligomers, including potentially bound to further proteins, co-factors or molecules. Thus, cellular and/or serum TK1 material thereby includes the cellular and/or serum TK1 in its various forms.

In a particular embodiment, the method is a method for determining a level of serum TK1 material in a body sample.

In another embodiment, the method is a method for determining a level of cellular TK1 material in a body sample.

In a further embodiment, the method is a method for determining a level of cellular TK1 material and serum TK1 material in a body sample.

A further aspect of the embodiments relates to a kit for determining a level of cellular and/or serum TK1 material in a body sample. The kit comprises a first monoclonal antibody according to embodiments immobilized to a solid support or intended to be immobilized to the solid support. The kit also comprises a second monoclonal antibody according to the embodiments.

The first monoclonal antibody of the kit has specificity for a first epitope selected from a group consisting of GEAVAARKLF (SEQ ID NO: 2) of human TK1; at least one of NCPVPGKPGE (SEQ ID NO: 4), PVPGKPGEAV (SEQ ID NO: 5) and NCPVPGKPGEAV (SEQ ID NO: 3) of human TK1; and a conformation dependent epitope of human TK1. The second monoclonal antibody of the kit has specificity for a second, different epitope selected from the group.

Thus, the two monoclonal antibodies of the kit are both capable of binding to the serum form of human TK1 and preferably also to the cellular form of human TK1. However, the two monoclonal antibodies of the kit have specificity for different epitopes selected from the above presented group.

In an embodiment, the first monoclonal antibody has specificity to the first epitope selected from one of GEAVAARKLF (SEQ ID NO: 2) of human TK1 and the conformation dependent epitope of human TK1 and the second monoclonal antibody has specificity to the second epitope selected from the other of GEAVAARKLF (SEQ ID NO: 2) of human TK1 and the conformation dependent epitope of human TK1.

In another embodiment, the first monoclonal antibody has specificity to the first epitope selected from one of GEAVAARKLF (SEQ ID NO: 2) of human TK1 and at least one of NCPVPGKPGE (SEQ ID NO: 4), PVPGKPGEAV (SEQ ID NO: 5) and NCPVPGKPGEAV (SEQ ID NO: 3) of human TK1 and the second monoclonal antibody has specificity to the second epitope selected from the other of GEAVAARKLF (SEQ ID NO: 2) of human TK1 and at least one of NCPVPGKPGE (SEQ ID NO: 4), PVPGKPGEAV (SEQ ID NO: 5) and NCPVPGKPGEAV (SEQ ID NO: 3) of human TK1.

In a further embodiment, the first monoclonal antibody has specificity to the first epitope selected from one of at least one of NCPVPGKPGE (SEQ ID NO: 4), PVPGKPGEAV (SEQ ID NO: 5) and NCPVPGKPGEAV (SEQ ID NO: 3) of human TK1 and the conformation dependent epitope of human TK1 and the second monoclonal antibody has specificity to the second epitope selected from the other of at least one of NCPVPGKPGE (SEQ ID NO: 4), PVPGKPGEAV (SEQ ID NO: 5) and NCPVPGKPGEAV (SEQ ID NO: 3) of human TK1 and the conformation dependent epitope of human TK1.

In a first particular embodiment, the first monoclonal antibody is XPA 210-Ar1 and the second monoclonal antibody is XPA 210-Ar2. In a second particular embodiment, the first monoclonal antibody is XPA 210-Ar2 and the second monoclonal antibody is XPA 210-Ar1. In a third particular embodiment, the first monoclonal antibody is XPA 210-Ar1 and the second monoclonal antibody is XPA 210-Ar3. In a fourth particular embodiment, the first monoclonal antibody is XPA 210-Ar3 and the second monoclonal antibody is XPA 210-Ar1. In a fifth particular embodiment, the first monoclonal antibody is XPA 210-Ar2 and the second monoclonal antibody is XPA 210-Ar3. In a sixth particular embodiment, the first monoclonal antibody is XPA 210-Ar3 and the second monoclonal antibody is XPA 210-Ar2.

In a particular embodiment, the kit is a sandwich assay kit. This means that the kit uses monoclonal antibodies binding to different epitopes of cellular and/or serum TK1 material so that both the first and second monoclonal antibodies can simultaneously bind to the same cellular and/or serum TK1 complex or molecule.

In a particular embodiment, the kit is an Enzyme-Linked Immunosorbent Assay (ELISA) kit and preferably a sandwich ELISA.

A sandwich ELISA can be used to detect cellular and/or serum TK1 material in a body sample by preparing a surface of the solid support to which the first monoclonal antibody is bound as so-called capture antibody. In a preferred embodiment, a known quantity of the first monoclonal antibody is bound to the surface of the solid support. Any nonspecific binding sites on the surface are optionally but preferably blocked. The body sample is then applied to the surface so that any cellular and/or serum TK1 material present therein will be captured by the immobilized first monoclonal antibodies. Unbound material is preferably removed by one or multiple washing steps. The second monoclonal antibody is then added and is allowed to bind to any cellular and/or serum TK1 material captured by the first monoclonal antibody.

The amount of bound second monoclonal antibody is then determined in direct or indirection detection methods. For instance, a label or enzyme can be attached directly to the second monoclonal antibody or indirectly via a link, such as a biotin-streptavidin or a biotin-avidin link. It is, alternatively, possible to use a secondary antibody that is labeled or connected to an enzyme and binds specifically to the second monoclonal antibody.

Hence, in an embodiment the second monoclonal antibody has a covalently attached biotin. Alternatively, the second monoclonal antibody has a covalently attached streptavidin or avidin.

The kit preferably also comprises a horseradish peroxidase (HRP) labeled strepatividin or a HRP labeled avidin. Alternatively, the kit also comprises a HRP labeled biotin. The kit also comprises a HRP substrate, such as a 3,3',5,5'-tetramethylbenzidine (TMB) substrate, a 3,3'-diaminobenzidine (DAB) substrate or a 2,2'-azino-bis(3-ethylbenzothiazoline-6-sulphonic acid (ABTS) substrate. In such a case, the level of cellular and/or serum TK1 material in the body sample can be determined by spectrophotometric methods that detect the conversion of the chromogenic substrate by HRP into a colored product that is detectable.

Figure 3:
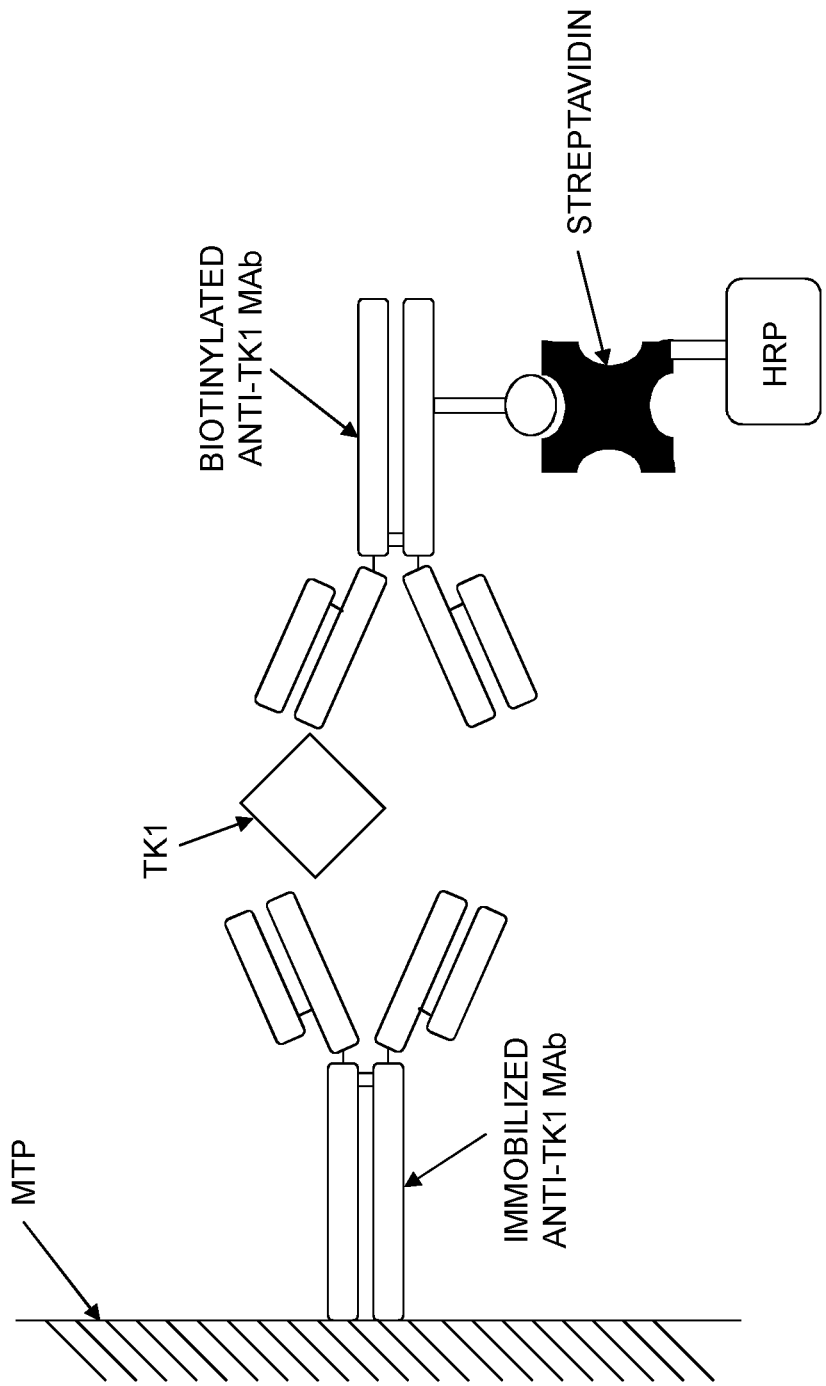
FIG. 3 is a schematic illustration of a design embodiment of a sandwich ELISA assay.

In an embodiment, the kit also comprises a microtiter plate (MCP) as the solid support to which the first monoclonal antibody is immobilized or is intended to be immobilized. FIG. 3 is a schematic overview of the concept of a sandwich ELISA using the first and second monoclonal antibodies according to an embodiment.

The kit does not necessarily have to be an ELISA kit. In another embodiment, the kit uses affinity chromatography where the first monoclonal antibody is bound to the stationary phase, such as to a gel matrix or beads in a column. For instance, the gel matrix or beads could be made of agarose, such as SEPHAROSE®.

In such a case, cellular and/or serum TK1 material present in a body sample will be entrapped in the column through binding to the immobilized first monoclonal antibodies. Following washing, the bound cellular and/or serum TK1 material can be eluded and detected using the second monoclonal antibody. For instance, the amount of eluded cellular and/or serum TK1 material can be determined using Western blotting and with the second monoclonal antibody for TK1 detection using direct or indirect detection methods.

The solid support could alternatively be magnetic beads, such as DYNABEADS®.

The kit of the present embodiments can be used in the previously described method for determining the level of cellular and/or serum TK1 material in a body sample.

A further aspect of the embodiments relates to a method for estimating the likelihood of recurrence of a tumor in a subject. The method comprises determining a level of serum TK1 material in a body sample from the subject using a method or a kit according to the embodiments. The level of serum TK1 material in the body sample is then compared with a level of serum TK1 material representative of a population of healthy subjects or with a level of serum TK1 material previously determined in the subject.

A determined level that is higher than a level associated with a population of healthy persons indicates an increased likelihood of recurrence of a tumor in the subject. Similarly, a determined level that is higher than a level associated with the subject subsequent to previous therapy indicates an increased likelihood of recurrence of a tumor in the subject. For more information of estimating the likelihood of tumor recurrence based on a determined level of TK1 material please refer to [24, 25].

Yet another aspect of the embodiments relates to a method for determining cell proliferation in a subject. The method comprises determining a level of serum TK1 material in a body sample from the subject using a method or a kit according to the embodiments. The method also comprises determining the cell proliferation based on the level of serum TK1 material in the body sample.

In a particular embodiment, a level of normal or tumor cell proliferation is determined and compared with the determined level of serum TK1 material to determine whether the subject has normal or baseline cell proliferation or an elevated cell proliferation.

The present method can be used as a tool in monitoring various therapies applied to subjects. For instance, the method can be used to monitor anti-proliferation or anti-tumor therapy in the subject. In such a case, the method can be used to verify whether a selected anti-proliferation or anti-tumor therapy has the desired effect in reducing cell proliferation in the subject. If the therapy does not have the desired effect, i.e. no significant decrease in cell proliferation is detected, then another or a modified anti-proliferation or anti-tumor therapy can instead be applied to the subject.

A further aspect of the embodiments relates to a method for determining a proliferation process response in a subject suffering from a malignant disease. The method comprises determining a level of serum TK1 material in a body sample from the subject using a method or a kit according to the embodiments. The method also comprises determining the proliferation process response based on the level of serum TK1 material in the body sample. An example of such a proliferation process response could be an immune reaction or immune reaction response. In an embodiment, at least one other biomarker for the proliferation process response may also be used in the determination.

Yet another aspect of the embodiments relates to a method for determining a level of inflammation, infection or tumor cell proliferation in a subject. The method comprises determining a level of serum TK1 material in a body sample from the subject using a method or a kit according to the embodiments. The method also comprises determining the level of inflammation, infection or tumor cell proliferation based on the level of serum TK1 material in the body sample. In an embodiment, at least one other biomarker for inflammation, infector or tumor cell proliferation may also be used in the determination.

Proliferation of tumor cells, such as breast tumor, lung tumor and bladder tumor, may be particularly determined and monitored according to the present method.

In the above described embodiments of methods and kits using monoclonal antibodies according to the embodiments the subject is preferably a human subject and the body sample is preferably selected from the previously described group of suitable body samples.

Further aspects of the embodiments relate to an isolated peptide consisting of the amino acid GEAVAARKLF (SEQ ID NO: 2), NCPVPGKPGE (SEQ ID NO: 4), PVPGKPGEAV (SEQ ID NO: 5) or NCPVPGKPGEAV (SEQ ID NO: 3). Such an isolated peptide is highly suitable as an epitope for antibody binding. The isolated peptide may be used for preparing a monoclonal anti-TK1 antibody or fragment that is capable of binding to the serum form of human TK1 and preferably also to human recombinant TK1 and the cellular form of human TK1.

Yet another aspect of the embodiments relates to a method of producing a monoclonal antibody capable of binding to a serum form of human TK1. The method comprises immunizing a non-human animal with a first peptide conjugate comprising a peptide having amino acid sequence GQPAGPDNKENCPVPGKPGEAVAARKLFAPQ (SEQ ID NO: 1) coupled to a first carrier protein or a second peptide conjugate comprising the peptide having amino acid sequence GQPAGPDNKENCPVPGKPGEAVAARKLFAPQ (SEQ ID NO: 1) coupled to a second carrier protein that is different from the first carrier protein. The method also comprises isolating splenocytes from the non-human animal with blood titers for the first peptide conjugate or the second peptide conjugate. The method further comprises forming hybridomas by fusing the splenocytes with myelomas. The method additionally comprises screening supernatant from hydridomas, resulting from immunization with the first peptide conjugate, for titers for the second peptide conjugate and screening supernatant from hybridomas, resulting from immunization with the second peptide conjugate, for titers for the first peptide conjugate. The method further comprises selecting a hybridoma producing a monoclonal antibody capable of binding to the first peptide conjugate, to the second peptide conjugate and to human rTK1. The method additionally comprises isolating the monoclonal antibody from supernatant of the selected hybridoma.

In an embodiment, selecting the hybridoma comprises selecting a hybridoma producing a monoclonal antibody capable of binding to the first peptide conjugate, to the second peptide conjugate, to human rTK1 and to a TK1 present in a serum sample obtained from a human subject suffering from cancer.

In an embodiment, the method comprises selecting an isolated monoclonal antibody capable of binding to a TK1 present in a serum sample obtained from a human subject suffering from cancer.

Thus, in a preferred embodiment the method involves a selection in order to obtain monoclonal antibodies that are capable of binding to the serum form of TK1. This selection can either be made by selecting hybridomas or by selecting among isolated monoclonal antibodies.

EXAMPLES

The present examples indicate the design and multi-step isolation of three unique monoclonal anti-TK1 antibodies. The monoclonal anti-TK1 antibodies are capable of recognizing recombinant TK, cellular TK1 and serum TK1. Furthermore, the immunization, selection and final screening procedure for obtaining the unique monoclonal anti-TK1 antibodies are disclosed, including their epitope binding regions in the TK1 amino acid sequence. The design and performance of a sandwich ELISA based on two of these monoclonal anti-TK1 antibodies with samples from healthy blood donors and from patients with different types of cancer disease are also described.

Example 1: Preparation of Mouse Monoclonal Antibodies Against the C-Terminal Region of Human TK1

The immunization and selection of mouse monoclonal antibodies against the C-terminal region of human TK1 with the following sequence GQPAGPDNKENCPVPGKPGEAVAARKLFAPQ (SEQ ID NO: 1), originating from the human TK1 protein sequence [19], was done at two occasions.

| | |
|---|---|
| XPA 210 | GQPAGPD---NKENC--PVPGKPGEAVAA---RKLFAPQ |
| HUMAN | KKASGQPAGPD---NKENC--PVPGKPGEAVAA---RKLFAPQQILQCS |
| MOUSE | KKSSAQTAGSD---NK-NC--LVLGQPGEALVV---RKLFASQQVLQYN |
| RAT | KKSSAQTA--D---NKENY--SVLGQPIEIPAV---RKLFAPQQILQCN |
| CHICK-EN | QKRPQQ-LGS---ENKENV--PMGVKQLDMPAS---RKIFAS |
| DOG | KASGPPMGLDSRENKENVLVLVPGKPGEGKEATGV RKLFAPQHVLQCS |

The above presented sequences show a comparison of the C-terminal region of human TK1 (SEQ ID NO: 21) and the sequence used for immunization with corresponding TK1 sequences in mouse (SEQ ID NO: 22), rat (SEQ ID NO: 23), chicken (SEQ ID NO: 24) and dog (SEQ ID NO: 25).

In the first approach female Balb/c mice were immunized with the peptide coupled to bovine serum albumin (BSA) by cross linking with glutaraldehyde (2.3%) by standard methods, using an equal amount of peptide and carrier protein. Mice were initially immunized with 200 μg conjugate (in Freunds complete adjuvans) and after three booster immunizations (100 µg each in Freunds incomplete adjuvans) splenocytes were isolated from mice with high blood titers for the antigen and fused with mouse myeloma cell line SP 2/0. The resulting hybridomas were subjected to multiple sets of sub-cloning and supernatants from the wells with cells were screened using an ELISA alkaline phosphate detection system (Vector Laboratories, CA, USA) with 96-well plates coated with the peptide antigen (0.05 µg/well, SEQ ID NO: 1). The supernatants with highest titers from positive wells were further sub-cloned in total three to five times and the supernatants were tested. Finally, seven candidate monoclonal hybridoma clones with high titers for the 31-mer peptide and human recombinant TK1 were identified. Cell stocks were established, the cultures were expanded and a large batch of supernatants was prepared, which were lyophilized and tested in the dot blot assay and the ELISA assay. This procedure led to the isolation of monoclonal antibody denoted XPA 210-Ar1 herein.

In the second approach to obtain monoclonal antibodies to the C-terminal peptide three different antigens were used: i) XPA 210 peptide (SEQ ID NO: 1) coupled to BSA as described above, ii) XPA 210 peptide coupled to keyhole limpet cyanine (KLH) with similar cross linking method and iii) human rTK1. The production and structural properties of rTK1 is described in [20]. Mice were initially immunized with 100 µg peptide conjugates or rTK1 in Freunds complete adjuvans and after three booster immunizations (100 µg each in Freunds incomplete adjuvans) splenocytes were isolated from mice with high blood titers for the antigen and fused with mouse myeloma cell line SP 2/0. The resulting hybridoma supernatants were screened using the system essentially as described above with 1 µg/well peptide antigen. The hybridoma supernatants resulting from immunization with the peptide BSA conjugate were screened with the peptide KHL conjugate in the wells and vice versa for the peptide KHL immunizations. This screening was designed to avoid antibodies produced against the carrier protein used in the respective immunizations. The supernatants with highest titers from positive wells were sub-cloned five times. Only hybridomas, which were positive for both the peptide conjugates and human rTK1 were selected. In case of recombinant TK1 immunizations only, the TK1 protein was used in the selection. In each case ten candidate monoclonal hybridoma clones with high titers for the peptide conjugates and rTK1 were identified. Cell stocks were established, the cultures were expanded and a large batch of supernatants was prepared, which were lyophilized and tested in several assay as described below.

In order to identify a monoclonal antibody pair that would be suitable for a sandwich ELISA procedure several secondary screening methods were used as described in the following examples.

Example 2: Dot Blot Enhanced Chemiluminescence (ECL) Immune Detection

This procedure was done essentially as described in [21]. In summary, 3 to 5 µl of peptides (3-300 µg per spot), human rTK1 (0.02-0.2 ng per spot) or serum samples were directly applied onto a nitrocellulose membrane. The membranes were blocked in Tris-buffered saline (TBS) with 10% non-fat milk for 4 hours and incubated at room temperature (RT, 23-25° C.) over night after the addition of the supernatants or other primary anti-TK1 antibodies. After incubation with a biotinylated secondary anti-mouse IgG antibody for 1 hour at RT, the membrane was incubated in TBS buffer with avidin-HRP-streptavidin, followed by the addition of ECL substrate (GE Healthcare). The chemiluminescence intensity of a single spot on the membrane was detected on films (GE Healthcare) exposed for 2-4 min. Several serum samples were also applied to the membranes both from healthy controls and patients with different tumor diseases.

Only the hybridomas that clearly reacted with the peptide antigen, rTK1, sera from tumor patients with known high serum TK1 levels and minimally with sera from healthy persons, were high ranking candidates for further ELISA development. An example of these results is shown in FIG. 1 for antibodies XPA 210-Ar2 and XPA 210-Ar3.

Example 3: Immuno Affinity Magnetic Bead Assays

The assays were done in two steps. First the anti-XPA 210 antibodies selected based on the dot blot assay results (Example 2) were reacted with human rTK1 or a serum sample from a patient suffering from hematologic malignancies with high serum TK1 levels. In the second step magnetic-bead-containing anti-mouse IgG antibodies were added that bind to the antigen-antibody complexes, which subsequently could be removed from the reaction solution when the mixture was subjected to a magnetic field. The unbound TK1 protein was detected by an enzyme activity determination.

Human rTK1 at different concentrations (10 ng, 5 ng) and 30 µl serum from a patient with heamtologic cancer were diluted with 270 µl TBS Tween-20 (TBST)+2% BSA and combined with 4 µg of purified monoclonal anti-TK1 antibodies (dissolved in phosphate buffered saline (PBS)+0.1% BSA+2 mM ethylenediaminetetraacetic acid (EDTA), pH 7.4) or 50 µl of the respective supernatants from the selected hybridomas. These samples were then gently agitated for 2 hours at 4° C., followed by the addition of 70 µl of pre-washed sheep anti-mouse magnetic (Dyna) beads in wash buffer (PBS+0.1% BSA+2 mM EDTA, pH 7.4) and a further incubation for 1 hour. The sample tubes were then placed on the magnet for 2 min and 20 µl of the unbound material was removed and the TK1 activity measured. TK1 activity was determined with a modified $^3$H-Thd assay as described in [22]. The activity in the unbound fraction was compared to that of control samples treated with beads, which were not reacted with any hybridoma supernatants. The results with supernatants from nine selected hybridomas are shown in Table 1.

Most of the selected antibodies reacted with human rTK1, and bound as expected a major part of the TK1 activity, but in case of the interaction with serum TK1 in the patient sample there was a large range of TK1 activities remaining unbound (from 97 to 31%). Based on the latter results five candidate hybridomas were selected, expanded and larger amounts of IgG isolated and purified. These candidate antibodies were then tested in the assays described in the following example.

TABLE 1

| TK1 activity not bound to antibody-beads | | | |
|---|---|---|---|
| | Human rTK1 (10 ng) | Human rTK1 (5 ng) | Cancer serum |
| XPA 210-Ar1 | 66% | 52% | 31% |
| XPA 210-Ar64 | 26% | 23% | 32% |
| Sup-553 | 35% | 25% | 70% |
| Sup-168 | 82% | 64% | 86% |

TABLE 1-continued

| | TK1 activity not bound to antibody-beads | | |
|---|---|---|---|
| | Human rTK1 (10 ng) | Human rTK1 (5 ng) | Cancer serum |
| Sup-555 | 35% | 27% | 67% |
| Sup-139 | 47% | 30% | 97% |
| Sup-162 | 39% | 23% | 54% |
| Sup-583 | 31% | 21% | 58% |
| Sup-165 | 53% | 45% | 42% |

Example 4: Epitope Mapping Analysis with Monoclonal Anti-TK1 Antibody Candidates In order to determine the amino acid region to which the selected monoclonal antibodies bind a Pepscan analysis with biotinylated 10 amino acid target peptides was carried out. The procedure is based on synthesis of a set of 14 ten-mer amino acid peptides representing the region from 193 to 226 of the TK1 sequence as shown in connection with Example 1. Each peptide has an eight amino acids overlap and two amino acids gaps, leading to a set of 14 different peptides, see Table 2. The entire full-length peptide is also included and all these peptides were immobilized on a streptavidine coated microtiter plate. After a 1 hour adsorption step the plates were washed with PBS, 1% BSA and 0.1% Tween 20. The different antibodies were then added at approximately 5 μg/ml and the plates were incubated for 1 hour, followed by washing three times. Then a HRP conjugate was added and incubated for 1 hour. The plates were then washed six times with the same buffer. Finally the absorbance was determined with 100 μl 3,3',5,5'-tetramethylbenzidine (TMB) substrate and the results from one test with a series of antibodies are shown in Table 2.

TABLE 2

| | absorbance values at 415 nm for well containing antibodies | | | |
|---|---|---|---|---|
| Peptide | XPA 210-Ar1 | Sup-553 | Sup-165 | Sup-2119 |
| ASGQPAGPDN (SEQ ID NO: 26) | 0.113 | 0.067 | 0.057 | 0.063 |
| GQPAGPDNKE (SEQ ID NO: 27) | 0.108 | 0.061 | 0.057 | 0.057 |
| PAGPDNKENC (SEQ ID NO: 28) | 0.120 | 0.060 | 0.055 | 0.057 |
| GPDNKENCPV (SEQ ID NO: 29) | 0.112 | 0.064 | 0.060 | 0.057 |
| DNKENCPVPG (SEQ ID NO: 30) | 0.108 | 0.059 | 0.059 | 0.058 |
| KENCPVPGKP (SEQ ID NO: 31) | 0.109 | 0.060 | 0.058 | 0.057 |
| NCPVPGKPGE (SEQ ID NO: 4) | 0.114 | 0.062 | 1.988 | 0.058 |
| PVPGKPGEAV (SEQ ID NO: 5) | 0.115 | 0.063 | 1.838 | 0.057 |
| PGKPGEAVAA (SEQ ID NO: 32) | 0.112 | 0.071 | 0.059 | 0.058 |
| KPGEAVAARK (SEQ ID NO: 33) | 0.116 | 0.067 | 0.059 | 0.058 |
| GEAVAARKLF (SEQ ID NO: 2) | 3.507 | 0.065 | 0.057 | 0.058 |
| AVAARKLFAP (SEQ ID NO: 34) | 0.125 | 0.073 | 0.062 | 0.60 |
| AARKLFAPQQ (SEQ ID NO: 35) | 0.137 | 0.066 | 0.060 | 0.065 |
| ARKLFAPQQI (SEQ ID NO: 36) | 0.130 | 0.063 | 0.062 | 0.065 |
| XPA 210 (SEQ ID NO: 1) | 3.842 | 3.780 | 0.136 | 0.070 |
| | Sup-2115 | Sup-168 | Sup-1119 | Sup-584 |
| ASGQPAGPDN (SEQ ID NO: 26) | 0.058 | 0.063 | 0.063 | 0.066 |
| GQPAGPDNKE (SEQ ID NO: 27) | 0.058 | 0.057 | 0.061 | 0.060 |
| PAGPDNKENC (SEQ ID NO: 28) | 0.058 | 0.058 | 0.062 | 0.059 |
| GPDNKENCPV (SEQ ID NO: 29) | 0.059 | 0.061 | 0.062 | 0.060 |
| DNKENCPVPG (SEQ ID NO: 30) | 0.060 | 0.062 | 0.061 | 0.059 |
| KENCPVPGKP (SEQ ID NO: 31) | 0.061 | 0.061 | 0.063 | 0.058 |
| NCPVPGKPGE (SEQ ID NO: 4) | 0.062 | 1.235 | 0.061 | 0.059 |
| PVPGKPGEAV (SEQ ID NO: 5) | 0.062 | 1.093 | 0.065 | 0.060 |
| PGKPGEAVAA (SEQ ID NO: 32) | 0.062 | 0.065 | 0.064 | 0.062 |
| KPGEAVAARK (SEQ ID NO: 33) | 0.064 | 0.063 | 0.066 | 0.061 |

TABLE 2-continued absorbance values at 415 nm for well containing antibodies

| | | | | |
|---|---|---|---|---|
| GEAVAARKLF (SEQ ID NO: 2) | 0.062 | 0.067 | 0.064 | 0.470 |
| AVAARKLFAP (SEQ ID NO: 34) | 0.064 | 0.067 | 0.067 | 0.066 |
| AARKLFAPQQ (SEQ ID NO: 35) | 0.059 | 0.066 | 0.065 | 0.065 |
| ARKLFAPQQI (SEQ ID NO: 36) | 0.062 | 0.064 | 0.066 | 0.097 |
| XPA 210 (SEQ ID NO: 1) | 0.075 | 0.129 | 2.978 | 3.756 |

| | Sup-583 | Sup-162 |
|---|---|---|
| ASGQPAGPDN (SEQ ID NO: 26) | 0.060 | 0.067 |
| GQPAGPDNKE (SEQ ID NO: 27) | 0.061 | 0.064 |
| PAGPDNKENC (SEQ ID NO: 28) | 0.062 | 0.063 |
| GPDNKENCPV (SEQ ID NO: 29) | 0.062 | 0.063 |
| DNKENCPVPG (SEQ ID NO: 30) | 0.062 | 0.063 |
| KENCPVPGKP (SEQ ID NO: 31) | 0.060 | 0.063 |
| NCPVPGKPGE (SEQ ID NO: 4) | 0.060 | 0.064 |
| PVPGKPGEAV (SEQ ID NO: 5) | 0.060 | 0.067 |
| PGKPGEAVAA (SEQ ID NO: 32) | 0.061 | 0.067 |
| KPGEAVAARK (SEQ ID NO: 33) | 0.062 | 0.072 |
| GEAVAARKLF (SEQ ID NO: 2) | 0.276 | 0.072 |
| AVAARKLFAP (SEQ ID NO: 34) | 0.065 | 0.077 |
| AARKLFAPQQ (SEQ ID NO: 35) | 0.063 | 0.066 |
| ARKLFAPQQI (SEQ ID NO: 36) | 0.063 | 0.063 |
| XPA 210 (SEQ ID NO: 1) | 3.606 | 3.788 |

The results in Table 2 permits the identification of the minimal amino acid sequence required for binding of the various antibodies. It seems clear that there are three main types of antibody producing hybridomas selected for by the above procedure when the 31-mer peptide (XPA 210) was used as antigen.

One type, exemplified by XPA 210-Ar1, Sup-584 and Sup-583, binds to the region: GEAVAARKLF (SEQ ID NO: 2) and these amino acids would thus be included in the antigenic domain.

Another domain, exemplified by Sup-165 (XPA 210-Ar3) and Sup-168, binds to peptide 7 (NCPVPGKPGE (SEQ ID NO: 4)) and peptide 8 (PVPGKPGEAV (SEQ ID NO: 5)) encompassing amino acids NCPVPGKPGEAV (SEQ ID NO: 3) as the most likely antigenic domain. These antibodies apparently prefer the 10 amino acid peptides since the reactivity with the 31-mer XPA 210 is lower than for the first type.

Finally, there is a group, exemplified by Sup-553, Sup-1119 and Sup-162 (XPA 210-Ar2), which did not show any distinct binding to any of the fourteen 10-mer peptides. This result strongly suggest that their binding is conformation dependent, consisting of several regions that are not adjacent in the primary sequence but formed by a certain 3D conformation of the antigen domain.

Furthermore, the antibodies in this group, as well as the two other groups, all reacted with the full-length 31-mer peptide (XPA 210) as well as with human rTK1.

Figure 2:
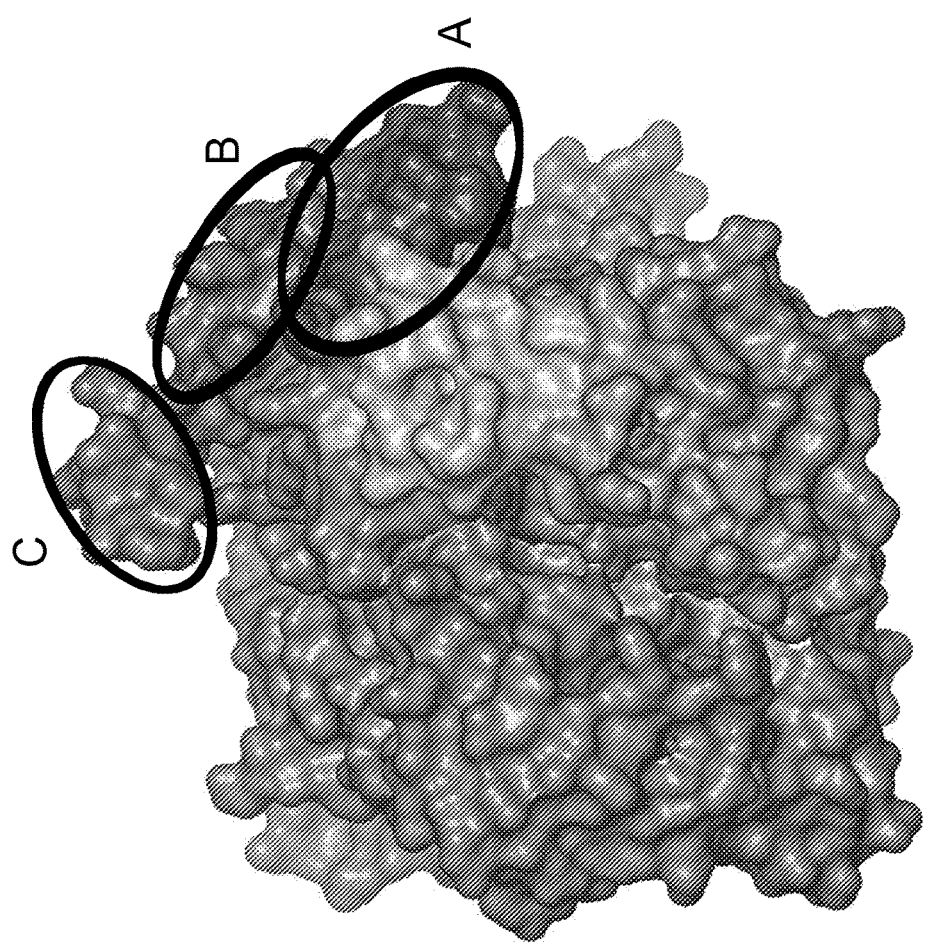
FIG. 2 illustrates a structural model for the C-terminal region of TK1 in a tetramer complex based on sequence similarities and the 3D structure of U. ureolyticum/pavreum (current nomenclature) and human TK1 [19, 20]. The region labeled A represents amino acid 195-207. The region labeled B represents amino acids 208-216, which most likely includes bend regions. The region labeled C, i.e. amino acids 215-222, contains a predicted C-terminal alfa helix close to the end of the protein. The A, B and C regions are likely to be exposed towards the surface of the enzyme complex and, thus, could be suitable antigenic sites for antibody production.

Thus, the data strongly indicate that the monoclonal antibody XPA 210-Ar1 recognizes a domain in the C-terminal part of the 31-mer (XPA 210). Secondary sequence predictions suggest that this region forms an alfa helix. Unfortunately, there is no direct structural data for this region of the TK1 tetramer, but a model based on sequence and structure homologies between the bacterial *Ureoplasma ureolyticum/pavrum* TK1 structure [20] and that of human rTK1, suggest a C-terminal structure as shown in FIG. 2. The overall XPA 210 region is most likely a turn region (labeled B in FIG. 2) with an alfa helix in the C-terminal (labeled C in FIG. 2). A possible interpretation of the epitope mapping results is that the XPA 210-Ar1 like epitope is related to the C-terminal alfa helix, the XPA 210-Ar3 epitope to the bending domain, very close to the KEN sequence that serves as the ubiqutinylation signal sequence for cell cycle degradation of TK1 [15]. Finally, the XPA 210-Ar2 epitope is conformation dependent and may be formed by different regions of the whole 3D structure of the 31-mer region. Thus, it is likely that monoclonal antibodies with different binding properties are likely to form suitable sandwich immune assay pairs.

Example 5: Sandwich ELISA Assay

The outline of a sandwich ELISA assay is shown in FIG. 3 with a first monoclonal anti-TK1 antibody bound to the wells of a microtiter plate (MTP), serving as a "catcher" interacting with the sample. A second monoclonal anti-TK1 antibody is added in a second step and binds to TK1 present in the sample and bound to the first monoclonal anti-TK1 antibody immobilized in the well. The second monoclonal anti-TK1 antibody is modified by biotinylation, which means that it can very efficiently interact with a reporter complex, in terms of HRP labeled streptavidin, producing a color reaction, which can be easily measured. A summary of the standard procedure in the sandwich ELISA assay is presented below:

1. Pipette equal volumes (70 µl) of sample and sample dilution buffer in a vial and vortex;
2. Incubate for 30 minutes at 23-25° C.;
3. Add 100 µl/well of the mixture of the sample and the sample dilution buffer;
4. Incubate for 2 hours with shaking at 650 rpm at 25° C.;
5. Wash four times with 350 µl PBS Tween-20 (PBST);
6. Add 100 µl/well of biotin labeled anti-TK1 antibody in reagent buffer;
7. Incubate for 1 hour with shaking at 650 rpm at 25° C.;
8. Wash four times with 350 µl PBST;
9. Add 100 µl/well of streptavidin poly-HRP;
10. Incubate for 30 minutes with shaking at 650 rpm at 25° C.;
11. Wash four times with 350 µl PBST;
12. Add 100 µl/well of TMB substrate;
13. Incubate for 15 minutes;
14. Add 100 µl/well of stop solution; and
15. Read absorbance at 450 nm.

In an initial test set-up, the monoclonal antibody XPA 210-Ar1 was selected as "catcher" with a polyclonal anti-XPA 210 antibody produced in chickens as detector [13, 23]. This set-up was used to verify that the sandwich ELISA could be designed as shown in FIG. 3. Thereafter, the polyclonal anti-XPA 210 antibody was replaced by a second monoclonal anti-TK1 antibody selected as disclosed herein.

In a first assay for selecting a second monoclonal antibody the purified new candidate antibodies from Example 4 were adsorbed to the MTP wells as catcher and the XPA 210-Ar1 antibody was used as detector. The results showed that there were only two supernatants of the candidate antibodies that gave positive results with serum from cancer patients: Sup-162 (XPA 210-Ar2) and Sup-165 (XPA 210-Ar3), while all five of candidate antibodies reacted with the 31-mer peptide (XPA 210) conjugate as well as with human rTK1. The highest reactivity was observed with XPA 210-Ar2 and large preparation of this antibody was produced, biotinylated and used as detector antibody. XPA 210-Ar1 was used as the catcher antibody in the XPA 210 ELISA (FIG. 3). The final results with this assay and various clinical samples are shown in Example 6.

Example 6: Sensitivity and Specificity of Sandwich ELISA Assay

Figure 4:
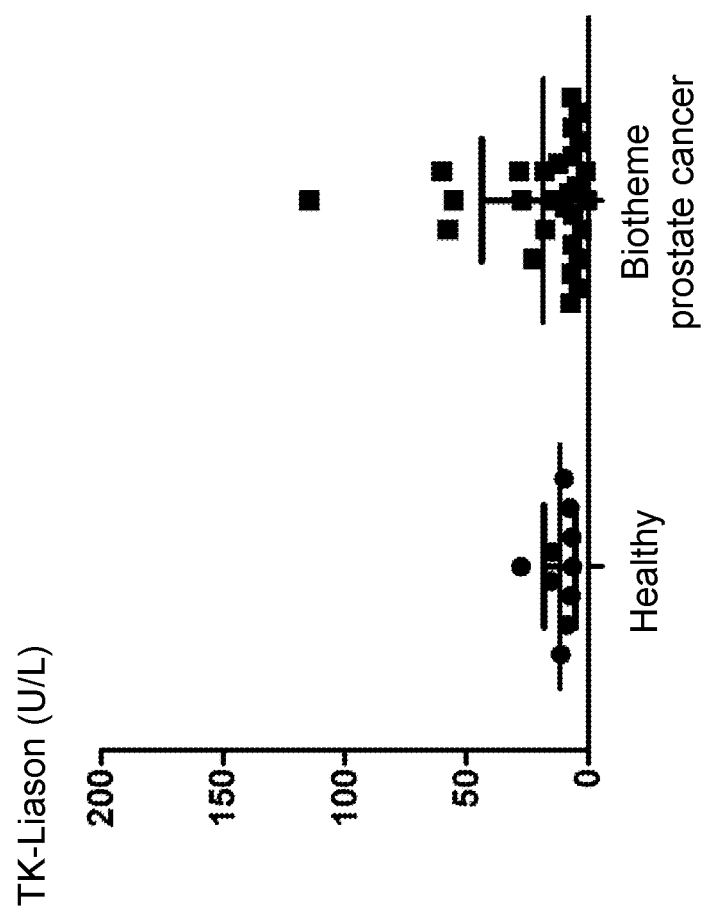
FIG. 4 illustrates TK activity values for sera from 10 healthy blood donors and 28 patients with diagnosed prostate cancer determined with the TK LIAISON® assay (Dia-Sorin Inc.).
Figure 5:
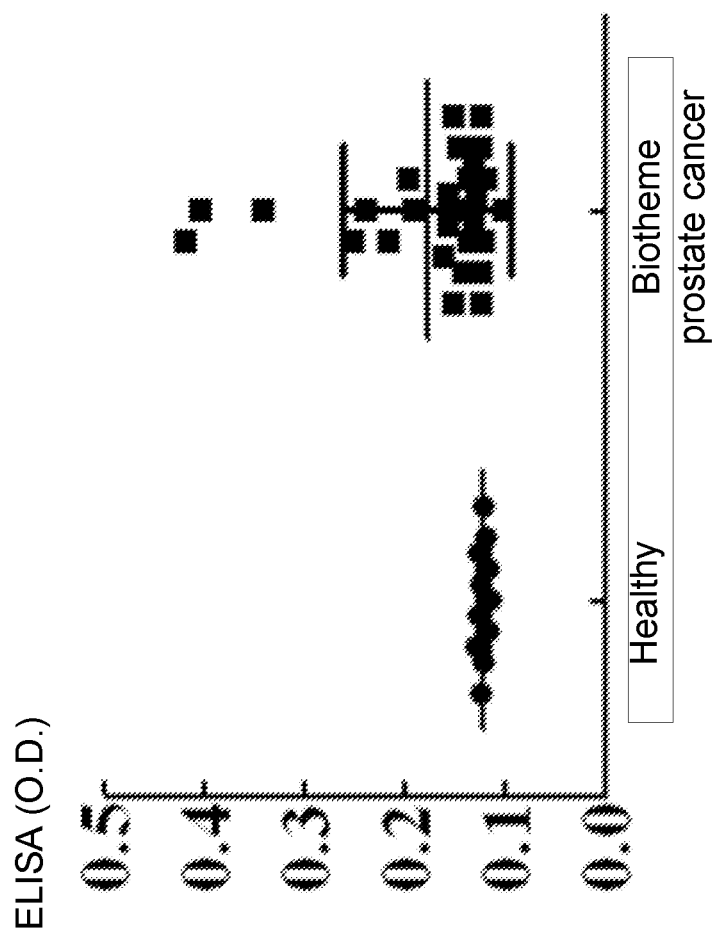
FIG. 5 illustrates absorbance values for sera from 10 healthy blood donors and 28 patients with diagnosed prostate cancer determined with a sandwich ELISA assay based on XPA 210-Ar1 and XPA 210-Ar2 antibodies.

Herein the results obtained with a prototype ELISA performed as described in Example 5 with the XPA 210-Ar1 and XPA-Ar2 monoclonal antibodies are presented. The samples tested were 28 sera from prostate cancer patients with different stages of disease (purchased from Biotheme Inc). As reference method the TK LIAISON® activity assay was used and the results are presented in FIG. 4. In FIG. 5 the results with ELISA assay are shown and in this case the direct absorbance values are presented.

The cut off value for the two assays was estimated by measuring the TK1 activity and protein levels in sera from 10 healthy blood donors with the TK LIAISON® assay and ELISA assay. The sensitivity of the TK LIAISON® assay at 90% specificity was calculated as 0.29. This means that with a cut off that allows one false in ten (based on the values from blood donors) the TK LIAISON® assay can identify 29% of the true positive (based on the values of the sera from cancer patients). In case of the ELISA assay, the sensitivity was 0.75. Thus, there is a significantly higher capacity of the ELISA assay to identify patients with solid tumor disease as compared to a TK1 activity assay measuring enzyme activity.

There was a significant correlation (r=0.85) between values obtained with the two assays when a combined group of 28 sera from prostate patients and 28 sera from breast cancer patients were tested in parallel. The existence of a high proportion of inactive serum TK1 in the blood of patients with solid tumors [17, 18] is most likely one explanation for the results described above.

Example 7: Sequencing of CDR Regions of Monoclonal Anti-TK1 Antibodies

Total RNA was extracted from frozen hybridoma cells and cDNA was synthesized from the RNA. RT-PCR was then performed to amplify the variable regions (heavy and light chains) of the antibodies, which were then cloned into a standard cloning vector separately and sequenced.

Total RNA was isolated from the hybridoma cells following the technical manual of TRIzol® Plus RNA Purification System (Invitrogen, Cat. No.: 15596-026). The total RNA was analyzed by agarose gel electrophoresis. In more detail, the isolated total RNA of the samples was run alongside a DNA marker Marker III (TIANGEN, Cat. No.: MD103) on a 1.5% agarose/GelRed™ gel. FIG. 6A illustrates the electrophoresis agarose gel of the DNA marker Marker III, whereas FIGS. 6B-6D illustrate the corresponding electrophoresis agarose gels with DNA marker Marker III (lane M) and total RNA of XPA 210-Ar1 (FIG. 6B), XPA 210-Ar2 (FIG. 6C) and XPA 210-Ar3 (FIG. 6D) producing hybridoma cells.

Total RNA was reverse transcribed into cDNA using isotype-specific anti-sense primers or universal primers following the technical manual of SuperScript™ III First-Strand Synthesis System (Invitrogen, Cat. No.: 18080-051). The antibody fragments of VH and VL were amplified according to the standard operating procedure of RACE of GenScript.

Figure 7C:
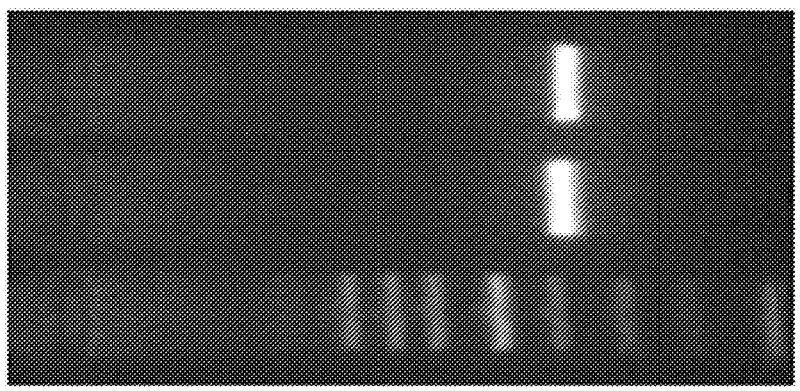
FIGS. 7A-7C illustrate agarose gel electrophoresis of PCR products of XPA 210-Ar1 (FIG. 7A), XPA 210-Ar2 (FIG. 7B) and XPA 210-Ar3 (FIG. 7C) producing hybridoma cells. Lane M, DNA marker Marker III, Lane 1, VH and Lane 2, VL.
Figure 7B:
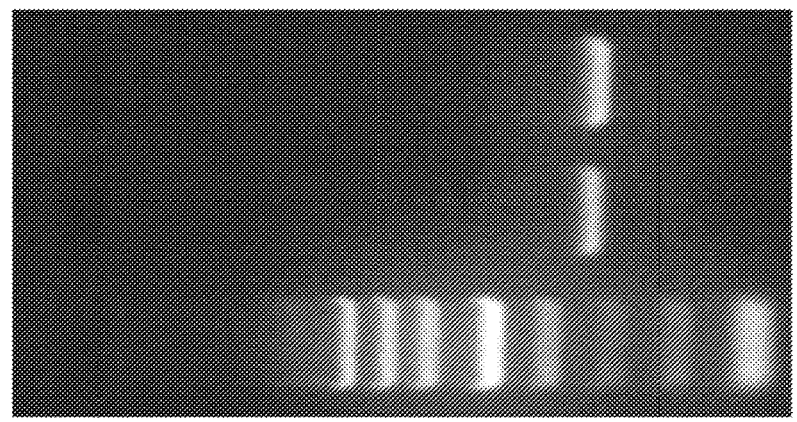
Figure 7A:
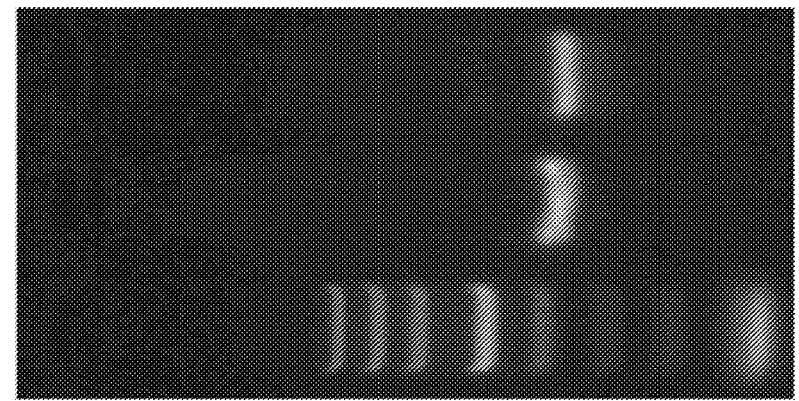

In more detail, 4 µl of the PCR products of each sample were run alongside the DNA marker Marker III on a 1.5% agarose/GelRed™ gel as shown in FIGS. 7A-7C. The PCR products were purified and stored at −20° C. until further use. Lane M in FIGS. 7A-7C indicates the DNA marker Marker III, whereas lane 1 and 2 correspond to the VH and VL fragments, respectively, of XPA 210-Ar1 (FIG. 7A), XPA 210-Ar2 (FIG. 7B) and XPA 210-Ar3 (FIG. 7C).

Amplified antibody fragments were separately cloned into a standard cloning vector using standard molecular cloning procedures.

Colony PCR screening was performed to identify clones with inserts of correct sizes. No less than five single colonies with inserts of correct sizes were sequenced for each antibody fragment. In more detail, five single colonies with correct VH and VL insert sizes were sent for sequencing. The VH and VL genes of five different clones were found nearly identical. The consensus sequences, listed below, are believed to be the sequence of the antibody produced by the respective hybridoma cells.

XPA 210-Ar1

Heavy chain: DNA sequence (405 bp)
Leader sequence-FR1-CDR1-FR2-CDR2-FR3-CDR3-FR4
SEQ ID NO: 37
<u>ATGGAATGGAGCTGGGTCTTTCTCTTCCTCCTGTCAGTAACTGCAGGT</u>

<u>GTCCAATCC</u>CAGGTTCAACTGCAGCAGTCTGGGGCTGAGCTGGTGAGG

CCTGGGGCTTCAATGAAGCTGTCCTGCAAGGCTTTGGGCTACACATTA

ACTGACTATGAAATGCACTGGGTGAAACAGACACCTGCGCATGGCCTG

GAATGGATTGGAGCTATTCATCCAGGATATGGTGGTACTGCCTATAAT

CAGAAGTTCAAGGGCAAGGCCACACTGACTGCAGACAAATCCTCCAGC

ACAGCCTACATGGAGCTCAGCAGCCTGACATCTGAGGACTCTGCTGTC

TATTACTGTACAACTTTTATTACTAAATTTGACTACTGGGGCCAAGGC

ACCACTCTCACAGTCTCCTCA

Heavy chain: Amino acids sequence (135 aa)
Leader sequence-FR1-CDR1-FR2-CDR2-FR3-CDR3-FR4
SEQ ID NO: 38
<u>MEWSWVFLFLLSVTAGVQS</u>QVQLQQSGAELVRPGASMKLSCKALGYTL

TDYEMHWVKQTPAHGLEWIGAIHPGYGGTAYNQKFKGKATLTADKSSS

TAYMELSSLTSEDSAVYYCTTFITKFDYWGQGTTLTVSS

Light chain: DNA sequence (396 bp)
Leader sequence-FR1-CDR1-FR2-CDR2-FR3-CDR3-FR4
SEQ ID NO: 39
<u>ATGATGAGTCCTGCCCAGTTCCTGTTTCTCTTAGTGCTCTGGATTCGG</u>

<u>GAAACCAACGGT</u>GATGTTGTCCTGACCCAGACTCCACTCACTTTGTCG

GTAACCATTGGACAACCAGCCTCCATCTCTTGCAAGTCAAGTCAGAGC

CTCTTAGATAGTGATGGAAAGACTTTTTTGAATTGGTTGTTACAGAGG

CCAGGCCAGTCTCCAAAGCGTCTAATCTATCTGGTGTCTAAACTGGAC

TCTGGAGTCCCTGACAGGTTCACTGGCAGTGGATCAGGGACAGATTTC

ACACTGAGAATCAGCAGAGTGGAGGCTGAGGATTTGGGAGTTTATTAT

TGCTGGCAAGGTACACATTTTCCGTGGACGTTCGGTGGAGGCACCAAG

CTGGAAATCAAA

Light chain: Amino acids sequence (132 aa)
Leader sequence-FR1-CDR1-FR2-CDR2-FR3-CDR3-FR4
SEQ ID NO: 40
<u>MMSPAQFLFLLVLWIRETNG</u>DVVLTQTPLTLSVTIGQPASISCKSSQS

LLDSDGKTFLNWLLQRPGQSPKRLIYLVSKLDSGVPDRFTGSGSGTDF

TLRISRVEAEDLGVYYCWQGTHFPWTFGGGTKLEIK

XPA 210-Ar2

Heavy chain: DNA sequence (405 bp)
Leader sequence-FR1-CDR1-FR2-CDR2-FR3-CDR3-FR4
SEQ ID NO: 41
<u>ATGGAATGGAGCTGGGTCTTTCTCTTCCTCCTGTCAGTAACTGCAGGT</u>

<u>GTCCAATCC</u>CAGGTTCAACTGCAGCAGTCTGGGGCTGAGCTGGTGAGG

CCTGGGGCTTCAGTGAAACTGTCCTGCAAGGCTTTGGGCTACACATTT

ACTGACTATGAAATGCACTGGGTGAGGCAGACACCTGTGCATGGCCTG

GAATGGATTGGAGCTATTCTTCCAGGAAGTGGTGGTACTGCCTACAAT

CAGAAGTTCAAGGGCAAGGCCACACTGACTGCAGACAAATCCTCCAGC

ACAGCCTACATGGAGCTCAGCAGCCTGACATCTGAGGACTCTGCTGTC

TATTACTGTACTACTTTGATTACGACCTTTGACTACTGGGGCCAAGGC

ACCACTCTCACAGTCTCCTCA

Heavy chain: Amino acids sequence (135 aa)
Leader sequence-FR1-CDR1-FR2-CDR2-FR3-CDR3-FR4
SEQ ID NO: 42
<u>MEWSWVFLFLLSVTAGVQS</u>QVQLQQSGAELVRPGASVKLSCKALGYTF

TDYEMHWVRQTPVHGLEWIGAILPGSGGTAYNQKFKGKATLTADKSSS

TAYMELSSLTSEDSAVYYCTTLITTFDYWGQGTTLTVSS

Light chain: DNA sequence (396 bp)
Leader sequence-FR1-CDR1-FR2-CDR2-FR3-CDR3-FR4
SEQ ID NO: 43
<u>ATGATGAGTCCTGCCCAGTTCCTGTTTCTGTTAGTGCTCTGGATTCGG</u>

<u>GAAACCAACGGT</u>GATGTTGTGTTGACCCAGACTCCACTCACATTGTCG

GTTACCATTGGACAACCAGCCTCCATTTCTTGTAAGTCAAGTCAGAGC

CTCTTAGATAGTGATGGAAAGACATATTTGAATTGGTTGTTACAGAGG

CCAGGCCAGTCTCCAAAGCGCCTAATCTATCTGGTGTCTAAATTGGAC

TCTGGAGTCCCTGACAGGTTCACTGGCAGTGGATCAGGGACAGATTTC

ACACTGAAAATCAGCAGAGTGGAGGCTGAGGATTTGGGAGTTTATTAT

TGCTGGCAAGGTACACATTTTCCGTGGACGTTCGGTGGAGGCACCAAG

CTGGAAATCAAA

Light chain: Amino acids sequence (132 aa)
Leader sequence-FR1-CDR1-FR2-CDR2-FR3-CDR3-FR4
SEQ ID NO: 44
<u>MMSPAQFLFLLVLWIRETNG</u>DVVLTQTPLTLSVTIGQPASISCKSSQS

LLDSDGKTYLNWLLQRPGQSPKRLIYLVSKLDSGVPDRFTGSGSGTDF

TLKISRVEAEDLGVYYCWQGTHFPWTFGGGTKLEIK

XPA 210-Ar3

Heavy chain: DNA sequence (411 bp)
Leader sequence-FR1-CDR1-FR2-CDR2-FR3-CDR3-FR4
SEQ ID NO: 45
<u>ATGAGAGTGCTGATTCTTTTGTGCCTGTTCACAGCCTTTCCTGGTATC</u>

<u>CTGTCT</u>GATGTGCAGCTTCAGGAGTCAGGACCTGACCTGGTGAAACCT

TCTCAGTCACTTTCACTCACCTGCACTGTCACTGGCTACTCCATCACC

AGTGGTTATAGCTGGCACTGGATCCGGCAGTTTCCAGGAAACAAACTG

GAATGGTTGGGCTACATACACTATAGTGGTAGCACTACCTACAACCCA

TCTCTCAAAGGTCGGATCTCTATCACTCGAGACACATCCAAGAACCAG

TTCTTCCTGCAGTTGAATTCTGTGACTACTGAGGACACTGCCACATAT

TACTGTGCAAGATGGGGTACTGGCCACTGGTACTTCGATGTCTGGGCC

GCAGGGACCACGGTCACCGTCTCCTCA

Heavy chain: Amino acids sequence (137 aa)
Leader sequence-FR1-CDR1-FR2-CDR2-FR3-CDR3-FR4
SEQ ID NO: 46
<u>MRVLILLCLFTAFPGILS</u>DVQLQESGPDLVKPSQSLSLTCTVTGYSIT

SGYSWHWIRQFPGNKLEWLGYIHYSGSTTYNPSLKGRISITRDTSKNQ

FFLQLNSVTTEDTATYYCARWGTGHWYFDVWAAGTTVTVSS

-continued

Light chain: DNA sequence (384 bp)
Leader sequence-FR1-CDR1-FR2-CDR2-FR3-CDR3-FR4

SEQ ID NO: 47

ATGGCCTGGATTTCACTTATACTCTCTCTCCTGGCTCTCAGCTCAGGG

GCCATTTCCCAGGCTGTTGTGACTCAGGAATCTGCACTCACCACATCA

CCTGGTAAAACAGTCACACTCACTTGTCGCTCAAGTACTGGGGCTGTT

ACAACTACTAACTATGCCAACTGGGTCCAAGAAAAACCAGATCATTTA

TTCACTGGTCTAATAGGTGGTACCAACAACCGAGTTCCAGGTGTTCCT

GCCAGATTCTCAGGCTCCCTGATTGGAGACAAGGCTGCCCTCACCATC

ACAGGGGCACAGACTGAGGATGAGGCAATATATTTCTGTGCTCTATGG

TACAGCAACCATTGGGTGTTCGGTGGAGGAACCAAACTGACTGTCCTA

Light chain: Amino acids sequence (128 aa)
Leader sequence-FR1-CDR1-FR2-CDR2-FR3-CDR3-FR4

SEQ ID NO: 48

MAWISLILSLLALSSGAISQAVVTQESALTTSPGKTVTLTCRSSTGAV

TTTNYANWVQEKPDHLFTGLIGGTNNRVPGVPARFSGSLIGDKAALTI

TGAQTEDEAIYFCALWYSNHWVFGGGTKLTVL

Example 8: Isotype Identification of Monoclonal Anti-TK1 Antibody

Monoclonal anti-TK1 antibodies from hybridoma cell line XPA 210-Ar1 were used for isoptyping assay, which was performed following the technical manual of SBA Clonotyping™ System-HRP (SouthernBiotech, Cat. No.: 5300-05). The isotype of the monoclonal antibody XPA 210-Ar1 was determined to be IgG1 heavy chain and K light chain, see Table 3 below.

TABLE 3

Isotype identification of stock supernatants

|  | Isotype | Absorbance at 450 nm |
|---|---|---|
| Heavy chain | IgG1 | 1.604 |
|  | IgG2a | 0.168 |
|  | IgG2b | 0.134 |
|  | IgG3 | 0.138 |
|  | IgA | 0.150 |
|  | IgM | 0.133 |
| Light chain | K | 0.418 |
|  | λ | 0.153 |

The above-presented examples disclose the production and selection of a pair of monoclonal anti-TK1 antibodies that can be used to establish a routine in vitro diagnostic assay with sufficient specificity and sensitivity to be clinically relevant. The immunization, selection and characterization of such a pair of antibodies, XPA 210-Ar1 and XPA 210-Ar2, have been described and the performance of a prototype sandwich ELISA assay with samples from healthy blood donors and patients with breast and prostate cancer have produced promising results with higher sensitivity than that of the available TK Liaison assay.

The initial selection strategy was based on peptide conjugates with a selected region of TK1 representing the C-terminal domain, which is involved in the cell cycle regulation of the enzyme.

Three monoclonal antibodies have been selected and their unique property is that they bind efficiently to the serum form of human TK1. This is unique since several other antibodies can bind to the antigen peptides and to human rTK1 but only these three monoclonal antibodies could function in a sandwich immunoassay format using human serum.

Two of the antibodies were obtained with peptide-BSA conjugates (XPA 210-Ar1 and XPA 210-Ar3), while one (XPA 210-Ar2) was produced with the peptide-KLH conjugate. There were no antibodies having the desired characteristics found resulting from the immunization with human rTK1 that showed this capacity although four clones were initially selected. This result is in accordance with the fact that there are now several monoclonal anti-TK1 antibodies available commercially and still there is no assay developed for clinical use based on these antibodies.

Four of the commercial monoclonal antibodies (3B3.E11 from Abcam; M02, clone F12 from Abnova; EPR3194 and EPR3193, rabbit Mabs from Abnova) have been tested in a sandwich ELISA assay format described here, but none of them could react sufficiently with serum TK1. Therefore, the generation of suitable monoclonal antibodies based on rTK1 is apparently inefficient and may be related to the complex oligomeric structure of the TK1 protein found in the blood.

The unique nature of the monoclonal anti-TK1 antibodies described here is most likely in part due to their epitope binding properties, which is different and apparently complementing for efficient immune detection.

In the disclosed prototype ELISA assay XPA 210-Ar1 and XPA 210-Ar2 were used. Alternatively, one of these antibodies could be exchanged by XPA 210-Ar3. Furthermore, for an improved assay or for special applications of the immune assay it is very likely that availability of XPA 210-Ar3 will be very beneficial. The existence of these monoclonal anti-TK1 antibodies is one prerequisite for a functional ELISA assay.

Example 9: Binding Studies of the Interaction Between Recombinant TK1 and XPA 210-Ar1 and XPA 210-Ar2

In order to determine the binding characteristics of the interactions between recombinant TK1 and the two monoclonal antibodies used in the sandwich ELISA procedure preliminary binding studies were performed with surface resonance sensor technology, more specifically the Attana 200 dual channel continuous-flow system. This method is based on Quartz Crystal Microbalance technology, which provides highly biologically relevant information concerning the binding properties of antibody antigen interactions.

Figure 8A:
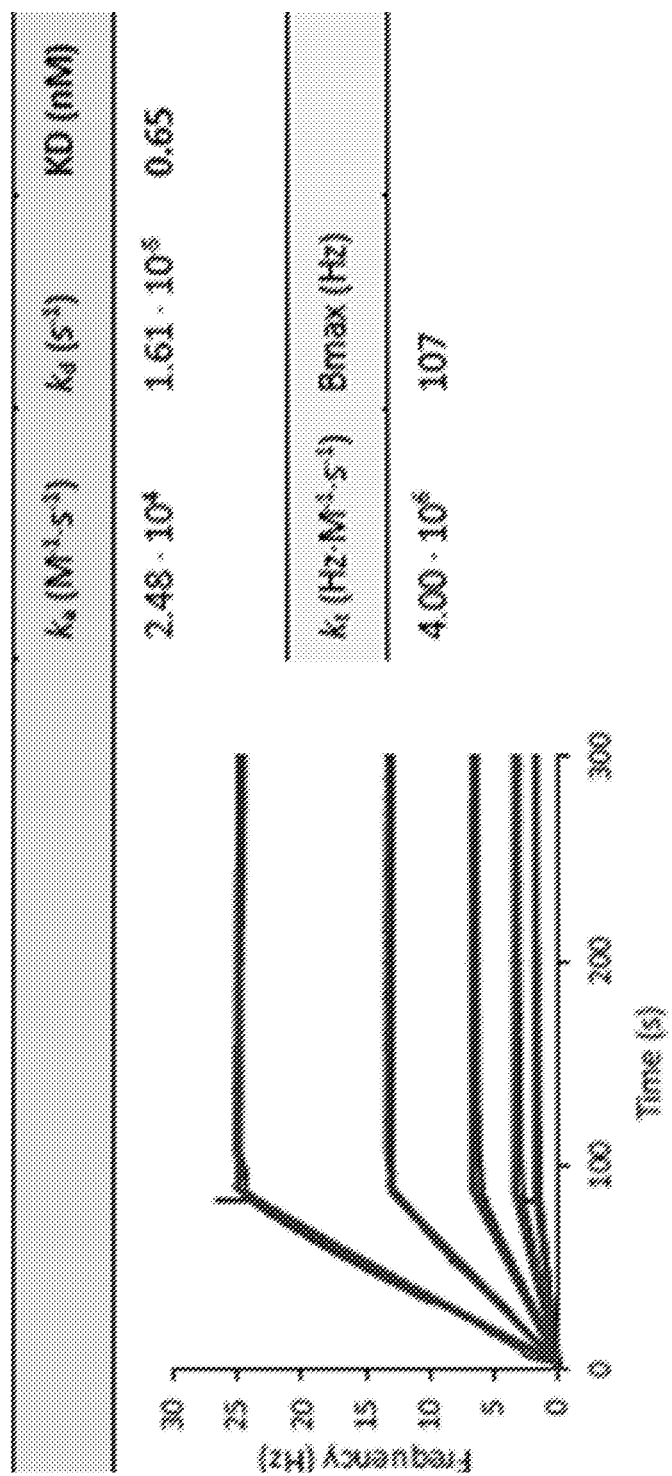
FIGS. 8A and 8B illustrate results from the Attana 2000 measurements of the interaction between recombinant human TK1 and XPA 210-Ar1 (FIG. 8A) and XPA 210-Ar2 (FIG. 8B). Curve fitting was done using a 1:1 binding model and the calculated constants are the association rate ($K_a$), the dissociation rate ($K_d$), the affinity (KD), the mass diffusion rate ($k_t$) and the maximum signal (Bmax).
Figure 8B:
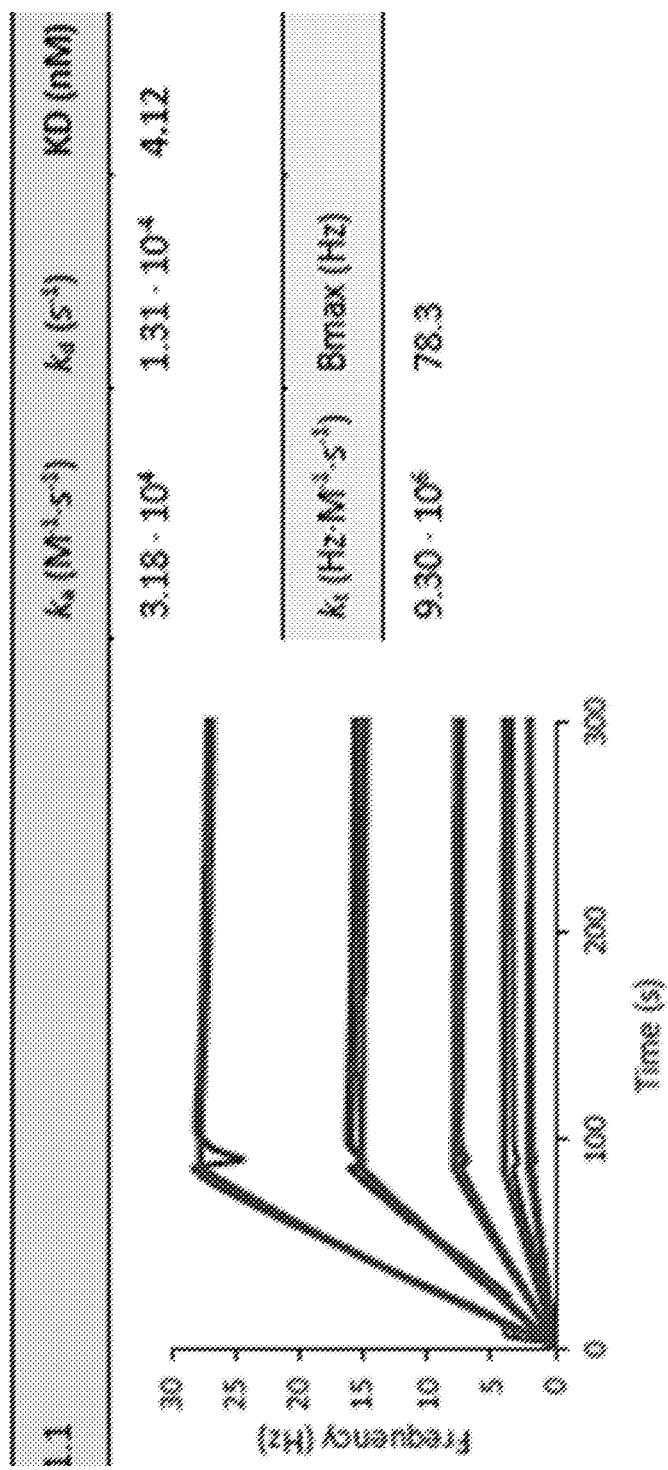

In the experiment shown in FIGS. 8A and 8B an LNB Carboxyl sensor chip was used, which was pre-reacted with the Mouse IgG capture kit (Biacore, GE Healthcare) with the amine coupling procedure. The ligands were XPA 210-Ar1 and XPA 210-Ar2 and they were captured to the surface with anti-mouse antibodies by two injections of 50 µg/ml antibody solutions in a 10 mM acetate buffer pH 4.5. An identically treated chip without the capture antibody was used a negative control. Pure recombinant TK1, diluted to 20 µg/ml in 10 mM HEPES, 150 mM NaCl, 0.005% Tween 20, pH 7.4, was injected over the surface at 25 µl/min. The association time was 84 s and the dissociation was measured for another 300 s. Buffer without recombinant TK1 was injected as a blank and subtracted from the sample injection signals.

The kinetic measurements were performed by a series of injections with five concentrations of recombinant TK1 from 20 µg/ml to 1.25 µg/ml and the results with XPA 210-Ar1 and XPA 210-Ar2 are shown in FIGS. 8A and 8B, respectively. An 1:1 binding model was used for calculation of the kinetic constants from the fitted curves of the double reference data as shown in FIGS. 8A and 8B. The results presented from the preliminary binding study demonstrated nanomolar (nM) affinity for recombinant TK1 with XPA 210-Ar1 (KD=0.65 nM) and XPA 210-Ar2 (KD=4.12 nM). The results further indicate that there seem to be a significantly stronger interaction between XPA 210-Ar1 and recombinant TK1 as compared to the interaction between XPA 210-Ar2 and recombinant TK1.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible.

REFERENCES

[1] Gronowitz, J. S., Hagberg, H., Kallander, C. F., Simonsson, B., 1983, The use of serum deoxythymidine kinase as a prognostic marker, and in the monitoring of patients with non-Hodgkin's lymphoma. *British Journal of Cancer* 47, 487-495.

[2] Karlstrom, A. R., Neumuller, M., Gronowitz, J. S., Kallander, C. F., 1990. Molecular forms in human serum of enzymes synthesizing DNA precursors and DNA. *Molecular and Cellular Biochemistry* 92, 23-35.

[3] He, Q. M., Skog, S., Wang, N. N., Eriksson, S., Tribukait, B., 1996. Characterization of a peptide antibody against a C-terminal part of human and mouse cytosolic thymidine kinase, which is a marker for cell proliferation. *European Journal of Cell Biology* 70, 117-124.

[4] Zhang, F., Li, H., Pendleton, A. R., Robison, J. G., Monson, K. O., Murray, B. K., O'Neill, K. L., 2001. Thymidine kinase 1 immunoassay: a potential marker for breast cancer. *Cancer Detectection and Prevention* 25, 8-15.

[5] He, Q., Zou, L., Zhang, P. A., Liu, J. X., Skog, S., Fornander, T., 2000. The clinical significance of thymidine kinase 1 measurement in serum of breast cancer patients using anti-TK1 antibody. *The International Journal of Biological Markers* 15, 139-146.

[6] Hallek, M., Langenmayer, I., Nerl, C., Knauf, W., Dietzfelbinger, H., Adorf, D., Ostwald, M., Busch, R., Kuhn-Hallek, I., Thiel, E., Emmerich, B., 1999. Elevated serum thymidine kinase levels identify a subgroup at high risk of disease progression in early, nonsmoldering chronic lymphocytic leukemia. *Blood* 93, 1732-1737.

[7] O'Neill, K. L., Zhang, F., Li, H., Fuja, D. G., Murray, B. K., 2007. Thymidine kinase 1—A prognostic and diagnostic indicator in ALL and AML patients. *Leukemia* 21, 560-563.

[8] von Euler, H., Eriksson, S., 2011. Comparative aspects of the proliferation marker thymidine kinase 1 in human and canine tumor diseases. *Veterinary and Comparative Oncology* 9, 1-15.

[9] Öhrvik, A., Lindh, M., Einarsson, R., Grassi, J., Eriksson, S., 2004. Sensitive nonradiometric method for determining thymidine kinase 1 activity. *Clinical Chemistry* 50, 1597-1606.

[10] He, Q., Fornander, T., Johansson, H., Johansson, U., Hu, G. Z., Rutqvist, L. E., Skog, S., 2006. Thymidine kinase 1 in serum predicts increased risk of distant or loco-regional recurrence following surgery in patients with early breast cancer. *Anticancer Research* 26, 4753-4759.

[11] He, Q. M., Zhang, P. G., Zou, L., Li, H. X., Wang, X. Q., Zhou, S., Fornander, T., Skog, S., 2005. Concentration of thymidine kinase 1 in serum (S-TK1) is a more sensitive proliferation marker in human solid tumors than its activity. *Oncology Reports* 14, 1013-1019.

[12] He, E., Xu, X. H., Guan, H., Chen, Y., Chen, Z. H., Pan, Z. L., Tang, L. L., Hu, G. Z., Li, Y., Zhang, M., Zhou, J., Eriksson, S., Fornander, T., Skog, S., 2010. Thymidine kinase 1 is a potential marker for prognosis and monitoring the response to treatment of patients with breast, lung, and esophageal cancer and non-Hodgkin's lymphoma. *Nucleosides, Nucleotides & Nucleic Acids.* 29, 352-358.

[13] Wu, C., Yang, R., Zhou, J., Bao, S., Zou, L., Zhang, P., Mao, Y., Wu, J., He, Q., 2003. Production and characterisation of a novel chicken IgY antibody raised against C-terminal peptide from human thymidine kinase 1. *Journal of Immunological Methods* 277, 157-169.

[14] Sherley, J. L., Kelly, T. J., 1988. Regulation of human thymidine kinase during the cell cycle. *Journal of Biological Chemistry* 263, 8350-8358.

[15] Ke, P. Y., Chang, C.-F., 2004. Mitotic degradation of human thymidine kinase 1 is dependent on the anaphase-promoting complex/cyclosome-CDH1-mediated pathway. *Molecular and. Cellular Biology* 24, 514-526.

[16] Eriksson, S., Munch-Petersen, B., Johansson, K., Eklund, H., 2002. Structure and function of cellular deoxyribonucleoside kinases. *Cellular and Molecular Life Sciences* 59, 1327-1346.

[17] Sharif, H., Kiran Kumar, J., Wang, L., He, E., Eriksson, S., 2012. Quaternary structures of recombinant, cellular, and serum forms of Thymidine Kinase 1 from dogs and humans. *BMC Biochemistry* 13, 12.

[18] Kiran Kumar J, Sharif, H., Westberg, S., von Euler, H., Eriksson, S., 2013. High levels of inactive thymidine kinase 1 polypeptide in sera from dogs with solid tumours by immunoaffinity methods: Implications for in vitro diagnostics. *The Veterinary Journal* 197, 854-860.

[19] Flemington, F., Bradshaw Jr., H. D., Traina-Dorge, V., Slagel, V., Deininger, P. L., 1987. Sequence, structure and promoter characterization of the human thymidine kinase gene. *Gene* 52, 267-277.

[20] Welin M, Kosinska U, Mikkelsen N E, Carnrot C, Zhu C, Wang L, Eriksson S, Munch-Petersen B, Eklund H, 2004. Structures of thymidine kinase 1 of human and mycoplasmic origin. *Proceedings of the National Academy of Sciences USA,* 101, 17970-17975.

[21] Wu, J. P., Mao, Y. R., Hu, L. X., Wang, N., Wu, C. J., He, Q., Skog, S., 2000. A new cell proliferating marker: Cytosolic thymidine kinase as compared to proliferating cell nuclear antigen in patients with colorectal carcinoma. *Anticancer Research* 20, 4815-4820.

[22] Sharif, H., von Euler, H., Westberg, S., He, E., Wang, L., Eriksson, S., 2012. A sensitive and kinetically defined radiochemical assay for canine and human serum thymidine kinase 1 (TK1) to monitor canine malignant lymphoma. *The Veterinary Journal* 194, 40-47.

[23] Gasparri, F., Wang, N., Skog, S., Galvani, A., Eriksson, S., 2009. Thymidine kinase 1 expression defines an activated G1 state of the cell cycle as revealed with site-specific antibodies and ArrayScan assays. *European Journal of Cell Biology* 88, 779-785.

[24] WO 2004/100760

[25] WO 2008/142664

[26] Munch-Petersen B., 2009. Reversible tetramerization of human TK1 to the high catalytic efficient form is induced by pyrophosphate, in addition to tripolyphosphates, or high enzyme concentration. *FEBS Journal* 276, 571-580

The invention claimed is:

1. A monoclonal antibody or a fragment of a monoclonal antibody capable of binding to a serum form of human thymidine kinase 1, TK1, wherein said monoclonal antibody or fragment
   (a) has specificity for an epitope GEAVAARKLF (SEQ ID NO: 2) of said human TK1, and has:
      a variable heavy, VH, domain complementarity determining region 1, CDR1 having amino acid sequence (SEQ ID NO: 6);
      a VH domain CDR2 having amino acid sequence (SEQ ID NO: 7);
      a VH domain CDR3 having amino acid sequence (SEQ ID NO: 8);
      a variable light, VL, domain CDR1 having amino acid sequence (SEQ ID NO: 9);
      a VL domain CDR2 having amino acid sequence (SEQ ID NO: 10); and
      a VL domain CDR3 having amino acid sequence (SEQ ID NO: 11);
   (b) has specificity for a conformation dependent epitope of said human TK1, and has:
      a VH domain CDR1 having amino acid sequence (SEQ ID NO: 6);
      a VH domain CDR2 having amino acid sequence (SEQ ID NO: 12);
      a VH domain CDR3 having amino acid sequence (SEQ ID NO: 13);

a VL domain CDR1 having amino acid sequence (SEQ ID NO: 14);
a VL domain CDR2 having amino acid sequence (SEQ ID NO: 10); and
a VL domain CDR3 having amino acid sequence (SEQ ID NO: 11);
or
(c) has specificity for at least one epitope selected from a group consisting of NCPVPGKPGE (SEQ ID NO: 4), PVPGKPGEAV (SEQ ID NO: 5) and NCPVPGK-PGEAV (SEQ ID NO: 3) of said human TK1, and has:
a VH domain CDR1 having amino acid sequence (SEQ ID NO: 15);
a VH domain CDR2 having amino acid sequence (SEQ ID NO: 16);
a VH domain CDR3 having amino acid sequence (SEQ ID NO: 17);
a VL domain CDR1 having amino acid sequence (SEQ ID NO: 18);
a VL domain CDR2 having amino acid sequence (SEQ ID NO: 19); and
a VL domain CDR3 having amino acid sequence (SEQ ID NO: 20).

2. The monoclonal antibody or fragment according to claim 1, wherein said monoclonal antibody or fragment is also capable of binding to human recombinant TK1 and to a cellular form of human TK1.

3. The monoclonal antibody or fragment according to claim 1, wherein said monoclonal antibody or fragment is capable of binding to a peptide having amino acid sequence GQPAGPDNKENCPVPGKPGEAVAARKLFAPQ (SEQ ID NO: 1).

4. The monoclonal antibody or fragment according to claim 1, obtainable by a process comprising:
immunizing a non-human animal with a first peptide conjugate comprising a peptide having amino acid sequence GQPAGPDNKENCPVPGKPGEAV-AARKLFAPQ (SEQ ID NO: 1) coupled to a first carrier protein or a second peptide conjugate comprising said peptide having amino acid sequence GQPAG-PDNKENCPVPGKPGEAVAARKLFAPQ (SEQ ID NO: 1) coupled to a second carrier protein that is different from said first carrier protein;
isolating splenocytes from said non-human animal with blood titers for said first peptide conjugate or said second peptide conjugate;
forming hybridomas by fusing said splenocytes with myelomas;
screening supernatant from hydridomas, resulting from immunization with said first peptide conjugate, for titers for said second peptide conjugate and screening supernatant from hydridomas, resulting from said immunization with said second peptide conjugate, for titers for said first peptide conjugate;
selecting a hybridoma producing monoclonal antibodies capable of binding to said first peptide conjugate, to said second peptide conjugate and to human recombinant TK1; and
isolating said monoclonal antibody from supernatant of said selected hybridoma.

5. A kit for determining a level of at least one of cellular TK1 and serum TK1 in a body sample, comprising:
a first monoclonal antibody according to claim 1 immobilized to a solid support; and
a second monoclonal antibody according to claim 1, wherein
said first monoclonal antibody has specificity for a first epitope selected from a group consisting of:
GEAVAARKLF (SEQ ID NO: 2) of human TK1;
at least one of NCPVPGKPGE (SEQ ID NO: 4), PVPGKPGEAV (SEQ ID NO: 5) and NCPVPGK-PGEAV (SEQ ID NO: 3) of said human TK1; and
a conformation dependent epitope of said human TK1; and
said second monoclonal antibody has specificity for a second, different epitope selected from said group.

6. The kit according to claim 5, wherein said kit is a sandwich assay kit.

7. The kit according to claim 5, wherein said kit is an Enzyme-Linked Immunosorbent Assay, ELISA, kit.

8. The kit according to claim 7, wherein said second monoclonal antibody has a covalently attached biotin or a covalently attached streptavidin or avidin.

9. The kit according to claim 8, further comprising:
a horseradish peroxidase, HRP, labeled streptavidin or avidin or a HRP labeled biotin; and
a HRP substrate selected from a group consisting of a 3,3',5,5'-tetramethylbenzidine, TMB, substrate, a 3,3'-diaminobenzidine, DAB, substrate and a 2,2'-azino-bis (3-ethylbenzothiazoline-6-sulphonic acid, ABTS, substrate.

10. The kit according to claim 5, further comprising a microtiter plate as said solid support.

11. The kit according to claim 5, further comprising agarose beads or magnetic beads as said solid support.

12. The kit according to claim 5, wherein
said first epitope to which said first monoclonal antibody has specificity is one of (i) GEAVAARKLF (SEQ ID NO: 2) of said human TK1, and (ii) said conformation dependent epitope of said human TK1, and
said second epitope to which said second monoclonal antibody has specificity is the other of (i) GEAV-AARKLF (SEQ ID NO: 2) of said human TK1, and (ii) said conformation dependent epitope of said human TK1.

13. A method for determining a level of at least one of cellular TK1 and serum TK1 in a body sample, comprising:
contacting said body sample with a monoclonal antibody or fragment according to claim 1; and
detecting an amount of bound monoclonal antibody or fragment.

14. The method according to claim 13, wherein said body sample is selected from a group consisting of a cell sample, a tissue sample, a blood sample, a serum sample, a cerebrospinal fluid sample, a pleural fluid sample, a synovial fluid sample and a peritoneal cavity fluid sample.

* * * * *

UNITED STATES PATENT AND TRADEMARK OFFICE
CERTIFICATE OF CORRECTION

PATENT NO. : 10,100,128 B2
APPLICATION NO. : 15/105999
DATED : October 16, 2018
INVENTOR(S) : Staffan Eriksson Page 1 of 1

It is certified that error appears in the above-identified patent and that said Letters Patent is hereby corrected as shown below:

On the Title Page

Item [30], change "1351531" to --1351531-7--.

Signed and Sealed this
Fourth Day of December, 2018

Andrei Iancu
*Director of the United States Patent and Trademark Office*

SEQUENCE LISTING

<160> NUMBER OF SEQ ID NOS: 48

<210> SEQ ID NO 1
<211> LENGTH: 31
<212> TYPE: PRT
<213> ORGANISM: Homo sapiens

<400> SEQUENCE: 1

Gly Gln Pro Ala Gly Pro Asp Asn Lys Glu Asn Cys Pro Val Pro Gly
 1               5                  10                  15

Lys Pro Gly Glu Ala Val Ala Ala Arg Lys Leu Phe Ala Pro Gln
            20                  25                  30

<210> SEQ ID NO 2
<211> LENGTH: 10
<212> TYPE: PRT
<213> ORGANISM: Homo sapiens

<400> SEQUENCE: 2

Gly Glu Ala Val Ala Ala Arg Lys Leu Phe
 1               5                  10

<210> SEQ ID NO 3
<211> LENGTH: 12
<212> TYPE: PRT
<213> ORGANISM: Homo sapiens

<400> SEQUENCE: 3

Asn Cys Pro Val Pro Gly Lys Pro Gly Glu Ala Val
 1               5                  10

<210> SEQ ID NO 4
<211> LENGTH: 10
<212> TYPE: PRT
<213> ORGANISM: Homo sapiens

<400> SEQUENCE: 4

Asn Cys Pro Val Pro Gly Lys Pro Gly Glu
 1               5                  10

<210> SEQ ID NO 5
<211> LENGTH: 10
<212> TYPE: PRT
<213> ORGANISM: Homo sapiens

<400> SEQUENCE: 5

Pro Val Pro Gly Lys Pro Gly Glu Ala Val
 1               5                  10

<210> SEQ ID NO 6
<211> LENGTH: 5
<212> TYPE: PRT
<213> ORGANISM: Mus musculus

<400> SEQUENCE: 6

Asp Tyr Glu Met His
 1               5

<210> SEQ ID NO 7
<211> LENGTH: 17
<212> TYPE: PRT
<213> ORGANISM: Mus musculus

<400> SEQUENCE: 7

Ala Ile His Pro Gly Tyr Gly Gly Thr Ala Tyr Asn Gln Lys Phe Lys
1               5                   10                  15

Gly

<210> SEQ ID NO 8
<211> LENGTH: 7
<212> TYPE: PRT
<213> ORGANISM: Mus musculus

<400> SEQUENCE: 8

Phe Ile Thr Lys Phe Asp Tyr
1               5

<210> SEQ ID NO 9
<211> LENGTH: 16
<212> TYPE: PRT
<213> ORGANISM: Mus musculus

<400> SEQUENCE: 9

Lys Ser Ser Gln Ser Leu Leu Asp Ser Asp Gly Lys Thr Phe Leu Asn
1               5                   10                  15

<210> SEQ ID NO 10
<211> LENGTH: 7
<212> TYPE: PRT
<213> ORGANISM: Mus musculus

<400> SEQUENCE: 10

Leu Val Ser Lys Leu Asp Ser
1               5

<210> SEQ ID NO 11
<211> LENGTH: 9
<212> TYPE: PRT
<213> ORGANISM: Mus musculus

<400> SEQUENCE: 11

Trp Gln Gly Thr His Phe Pro Trp Thr
1               5

<210> SEQ ID NO 12
<211> LENGTH: 17
<212> TYPE: PRT
<213> ORGANISM: Mus musculus

<400> SEQUENCE: 12

Ala Ile Leu Pro Gly Ser Gly Thr Ala Tyr Asn Gln Lys Phe Lys
1               5                   10                  15

Gly

<210> SEQ ID NO 13
<211> LENGTH: 7
<212> TYPE: PRT
<213> ORGANISM: Mus musculus

<400> SEQUENCE: 13

Leu Ile Thr Thr Phe Asp Tyr
1               5

<210> SEQ ID NO 14
<211> LENGTH: 16
<212> TYPE: PRT
<213> ORGANISM: Mus musculus

<400> SEQUENCE: 14

Lys Ser Ser Gln Ser Leu Leu Asp Ser Asp Gly Lys Thr Tyr Leu Asn
1               5                   10                  15

<210> SEQ ID NO 15
<211> LENGTH: 6
<212> TYPE: PRT
<213> ORGANISM: Mus musculus

<400> SEQUENCE: 15

Ser Gly Tyr Ser Trp His
1               5

<210> SEQ ID NO 16
<211> LENGTH: 16
<212> TYPE: PRT
<213> ORGANISM: Mus musculus

<400> SEQUENCE: 16

Tyr Ile His Tyr Ser Gly Ser Thr Thr Tyr Asn Pro Ser Leu Lys Gly
1               5                   10                  15

<210> SEQ ID NO 17
<211> LENGTH: 10
<212> TYPE: PRT
<213> ORGANISM: Mus musculus

<400> SEQUENCE: 17

Trp Gly Thr Gly His Trp Tyr Phe Asp Val
1               5                   10

<210> SEQ ID NO 18
<211> LENGTH: 14
<212> TYPE: PRT
<213> ORGANISM: Mus musculus

<400> SEQUENCE: 18

Arg Ser Ser Thr Gly Ala Val Thr Thr Thr Asn Tyr Ala Asn
1               5                   10

<210> SEQ ID NO 19
<211> LENGTH: 7
<212> TYPE: PRT
<213> ORGANISM: Mus musculus

<400> SEQUENCE: 19

Gly Thr Asn Asn Arg Val Pro
1               5

<210> SEQ ID NO 20
<211> LENGTH: 9
<212> TYPE: PRT
<213> ORGANISM: Mus musculus

<400> SEQUENCE: 20

Ala Leu Trp Tyr Ser Asn His Trp Val
1               5

<210> SEQ ID NO 21
<211> LENGTH: 41
<212> TYPE: PRT
<213> ORGANISM: Homo sapiens

<400> SEQUENCE: 21

-continued

Lys Lys Ala Ser Gly Gln Pro Ala Gly Pro Asp Asn Lys Glu Asn Cys
1               5                   10                  15

Pro Val Pro Gly Lys Pro Gly Glu Ala Val Ala Arg Lys Leu Phe
            20                  25                  30

Ala Pro Gln Gln Ile Leu Gln Cys Ser
        35                  40

<210> SEQ ID NO 22
<211> LENGTH: 40
<212> TYPE: PRT
<213> ORGANISM: Mus musculus

<400> SEQUENCE: 22

Lys Lys Ser Ser Ala Gln Thr Ala Gly Ser Asp Lys Asn Cys Leu
1               5                   10                  15

Val Leu Gly Gln Pro Gly Glu Ala Leu Val Val Arg Lys Leu Phe Ala
            20                  25                  30

Ser Gln Gln Val Leu Gln Tyr Asn
        35                  40

<210> SEQ ID NO 23
<211> LENGTH: 39
<212> TYPE: PRT
<213> ORGANISM: Rattus norvegicus

<400> SEQUENCE: 23

Lys Lys Ser Ser Ala Gln Thr Ala Asp Asn Lys Glu Asn Tyr Ser Val
1               5                   10                  15

Leu Gly Gln Pro Ile Glu Ile Pro Ala Val Arg Lys Leu Phe Ala Pro
            20                  25                  30

Gln Gln Ile Leu Gln Cys Asn
        35

<210> SEQ ID NO 24
<211> LENGTH: 33
<212> TYPE: PRT
<213> ORGANISM: Gallus gallus

<400> SEQUENCE: 24

Gln Lys Arg Pro Gln Gln Leu Gly Ser Glu Asn Lys Glu Asn Val Pro
1               5                   10                  15

Met Gly Val Lys Gln Leu Asp Met Pro Ala Ser Arg Lys Ile Phe Ala
            20                  25                  30

Ser

<210> SEQ ID NO 25
<211> LENGTH: 48
<212> TYPE: PRT
<213> ORGANISM: Canis lupus

<400> SEQUENCE: 25

Lys Ala Ser Gly Pro Pro Met Gly Leu Asp Ser Arg Glu Asn Lys Glu
1               5                   10                  15

Asn Val Leu Val Leu Val Pro Gly Lys Pro Gly Glu Gly Lys Glu Ala
            20                  25                  30

Thr Gly Val Arg Lys Leu Phe Ala Pro Gln His Val Leu Gln Cys Ser
        35                  40                  45

<210> SEQ ID NO 26
<211> LENGTH: 10

<212> TYPE: PRT
<213> ORGANISM: Homo sapiens

<400> SEQUENCE: 26

Ala Ser Gly Gln Pro Ala Gly Pro Asp Asn
1               5                   10

<210> SEQ ID NO 27
<211> LENGTH: 10
<212> TYPE: PRT
<213> ORGANISM: Homo sapiens

<400> SEQUENCE: 27

Gly Gln Pro Ala Gly Pro Asp Asn Lys Glu
1               5                   10

<210> SEQ ID NO 28
<211> LENGTH: 10
<212> TYPE: PRT
<213> ORGANISM: Homo sapiens

<400> SEQUENCE: 28

Pro Ala Gly Pro Asp Asn Lys Glu Asn Cys
1               5                   10

<210> SEQ ID NO 29
<211> LENGTH: 10
<212> TYPE: PRT
<213> ORGANISM: Homo sapiens

<400> SEQUENCE: 29

Gly Pro Asp Asn Lys Glu Asn Cys Pro Val
1               5                   10

<210> SEQ ID NO 30
<211> LENGTH: 10
<212> TYPE: PRT
<213> ORGANISM: Homo sapiens

<400> SEQUENCE: 30

Asp Asn Lys Glu Asn Cys Pro Val Pro Gly
1               5                   10

<210> SEQ ID NO 31
<211> LENGTH: 10
<212> TYPE: PRT
<213> ORGANISM: Homo sapiens

<400> SEQUENCE: 31

Lys Glu Asn Cys Pro Val Pro Gly Lys Pro
1               5                   10

<210> SEQ ID NO 32
<211> LENGTH: 10
<212> TYPE: PRT
<213> ORGANISM: Homo sapiens

<400> SEQUENCE: 32

Pro Gly Lys Pro Gly Glu Ala Val Ala Ala
1               5                   10

<210> SEQ ID NO 33
<211> LENGTH: 10
<212> TYPE: PRT
<213> ORGANISM: Homo sapiens

<400> SEQUENCE: 33

Lys Pro Gly Glu Ala Val Ala Ala Arg Lys
1               5                   10

<210> SEQ ID NO 34
<211> LENGTH: 10
<212> TYPE: PRT
<213> ORGANISM: Homo sapiens

<400> SEQUENCE: 34

Ala Val Ala Ala Arg Lys Leu Phe Ala Pro
1               5                   10

<210> SEQ ID NO 35
<211> LENGTH: 10
<212> TYPE: PRT
<213> ORGANISM: Homo sapiens

<400> SEQUENCE: 35

Ala Ala Arg Lys Leu Phe Ala Pro Gln Gln
1               5                   10

<210> SEQ ID NO 36
<211> LENGTH: 10
<212> TYPE: PRT
<213> ORGANISM: Homo sapiens

<400> SEQUENCE: 36

Ala Arg Lys Leu Phe Ala Pro Gln Gln Ile
1               5                   10

<210> SEQ ID NO 37
<211> LENGTH: 405
<212> TYPE: DNA
<213> ORGANISM: Mus musculus

<400> SEQUENCE: 37
atggaatgga gctgggtctt tctcttcctc ctgtcagtaa ctgcaggtgt ccaatcccag      60
gttcaactgc agcagtctgg ggctgagctg gtgaggcctg ggcttcaat gaagctgtcc     120 tgcaaggctt tgggctacac attaactgac tatgaaatgc actgggtgaa acagacacct    180
gcgcatggcc tggaatggat tggagctatt catccaggat atggtggtac tgcctataat    240
cagaagttca gggcaaggc cacactgact gcagacaaat cctccagcac agcctacatg     300
gagctcagca gcctgacatc tgaggactct gctgtctatt actgtacaac ttttattact    360
aaatttgact actggggcca aggcaccact ctcacagtct cctca                    405

<210> SEQ ID NO 38
<211> LENGTH: 135
<212> TYPE: PRT
<213> ORGANISM: Mus musculus

<400> SEQUENCE: 38

Met Glu Trp Ser Trp Val Phe Leu Phe Leu Leu Ser Val Thr Ala Gly
1               5                   10                  15

Val Gln Ser Gln Val Gln Leu Gln Gln Ser Gly Ala Glu Leu Val Arg
            20                  25                  30

Pro Gly Ala Ser Met Lys Leu Ser Cys Lys Ala Leu Gly Tyr Thr Leu
        35                  40                  45

Thr Asp Tyr Glu Met His Trp Val Lys Gln Thr Pro Ala His Gly Leu

```
            50                  55                  60
Glu Trp Ile Gly Ala Ile His Pro Gly Tyr Gly Thr Ala Tyr Asn
 65                  70                  75                  80

Gln Lys Phe Lys Gly Lys Ala Thr Leu Thr Ala Asp Lys Ser Ser
                 85                  90                  95

Thr Ala Tyr Met Glu Leu Ser Ser Leu Thr Ser Glu Asp Ser Ala Val
                100                 105                 110

Tyr Tyr Cys Thr Thr Phe Ile Thr Lys Phe Asp Tyr Trp Gly Gln Gly
            115                 120                 125

Thr Thr Leu Thr Val Ser Ser
        130                 135

<210> SEQ ID NO 39
<211> LENGTH: 396
<212> TYPE: DNA
<213> ORGANISM: Mus musculus

<400> SEQUENCE: 39
atgatgagtc ctgcccagtt cctgtttctc ttagtgctct ggattcggga aaccaacggt     60
gatgttgtcc tgacccagac tccactcact ttgtcggtaa ccattggaca accagcctcc    120
atctcttgca agtcaagtca gagcctctta gatagtgatg gaaagacttt tttgaattgg    180
ttgttacaga ggccaggcca gtctccaaag cgtctaatct atctggtgtc taaactggac    240
tctggagtcc ctgacaggtt cactggcagt ggatcaggga cagatttcac actgagaatc    300
agcagagtgg aggctgagga tttgggagtt tattattgct ggcaaggtac acattttccg    360
tggacgttcg gtggaggcac caagctggaa atcaaa                              396

<210> SEQ ID NO 40
<211> LENGTH: 132
<212> TYPE: PRT
<213> ORGANISM: Mus musculus

<400> SEQUENCE: 40

Met Met Ser Pro Ala Gln Phe Leu Phe Leu Leu Val Leu Trp Ile Arg
 1               5                  10                  15

Glu Thr Asn Gly Asp Val Val Leu Thr Gln Thr Pro Leu Thr Leu Ser
                 20                  25                  30

Val Thr Ile Gly Gln Pro Ala Ser Ile Ser Cys Lys Ser Ser Gln Ser
            35                  40                  45

Leu Leu Asp Ser Asp Gly Lys Thr Phe Leu Asn Trp Leu Leu Gln Arg
     50                  55                  60

Pro Gly Gln Ser Pro Lys Arg Leu Ile Tyr Leu Val Ser Lys Leu Asp
 65                  70                  75                  80

Ser Gly Val Pro Asp Arg Phe Thr Gly Ser Gly Ser Gly Thr Asp Phe
                 85                  90                  95

Thr Leu Arg Ile Ser Arg Val Glu Ala Glu Asp Leu Gly Val Tyr Tyr
            100                 105                 110

Cys Trp Gln Gly Thr His Phe Pro Trp Thr Phe Gly Gly Gly Thr Lys
        115                 120                 125

Leu Glu Ile Lys
        130

<210> SEQ ID NO 41
<211> LENGTH: 405
<212> TYPE: DNA
<213> ORGANISM: Mus musculus
```

<400> SEQUENCE: 41

```
atggaatgga gctgggtctt tctcttcctc ctgtcagtaa ctgcaggtgt ccaatcccag    60
gttcaactgc agcagtctgg ggctgagctg gtgaggcctg gggcttcagt gaaactgtcc   120
tgcaaggctt tgggctacac atttactgac tatgaaatgc actgggtgag gcagacacct   180
gtgcatggcc tggaatggat tggagctatt cttccaggaa gtggtggtac tgcctacaat   240
cagaagttca gggcaaggc cacactgact gcagacaaat cctccagcac agcctacatg   300
gagctcagca gcctgacatc tgaggactct gctgtctatt actgtactac tttgattacg   360
acctttgact actggggcca aggcaccact ctcacagtct cctca                   405
```

<210> SEQ ID NO 42
<211> LENGTH: 135
<212> TYPE: PRT
<213> ORGANISM: Mus musculus

<400> SEQUENCE: 42

```
Met Glu Trp Ser Trp Val Phe Leu Phe Leu Leu Ser Val Thr Ala Gly
1               5                   10                  15

Val Gln Ser Gln Val Gln Leu Gln Gln Ser Gly Ala Glu Leu Val Arg
            20                  25                  30

Pro Gly Ala Ser Val Lys Leu Ser Cys Lys Ala Leu Gly Tyr Thr Phe
        35                  40                  45

Thr Asp Tyr Glu Met His Trp Val Arg Gln Thr Pro Val His Gly Leu
    50                  55                  60

Glu Trp Ile Gly Ala Ile Leu Pro Gly Ser Gly Gly Thr Ala Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Thr Thr Leu Ile Thr Thr Phe Asp Tyr Trp Gly Gln Gly
        115                 120                 125

Thr Thr Leu Thr Val Ser Ser
    130                 135
```

<210> SEQ ID NO 43
<211> LENGTH: 396
<212> TYPE: DNA
<213> ORGANISM: Mus musculus

<400> SEQUENCE: 43

```
atgatgagtc ctgcccagtt cctgtttctg ttagtgctct ggattcggga aaccaacggt    60
gatgttgtgt tgacccagac tccactcaca ttgtcggtta ccattggaca accagcctcc   120
atttcttgta gtcaagtca gagcctctta gatagtgatg aaagacata tttgaattgg    180
ttgttacaga ggccaggcca gtctccaaag cgcctaatct atctggtgtc taaattggac   240
tctggagtcc ctgacaggtt cactggcagt ggatcaggga cagatttcac actgaaaatc   300
agcagagtgg aggctgagga tttgggagtt tattattgct ggcaaggtac acattttccg   360
tggacgttcg gtggaggcac caagctggaa atcaaa                              396
```

<210> SEQ ID NO 44
<211> LENGTH: 132
<212> TYPE: PRT
<213> ORGANISM: Mus musculus

<400> SEQUENCE: 44

Met Met Ser Pro Ala Gln Phe Leu Phe Leu Leu Val Leu Trp Ile Arg
1               5                   10                  15

Glu Thr Asn Gly Asp Val Val Leu Thr Gln Thr Pro Leu Thr Leu Ser
                20                  25                  30

Val Thr Ile Gly Gln Pro Ala Ser Ile Ser Cys Lys Ser Ser Gln Ser
            35                  40                  45

Leu Leu Asp Ser Asp Gly Lys Thr Tyr Leu Asn Trp Leu Leu Gln Arg
        50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
                100                 105                 110

Cys Trp Gln Gly Thr His Phe Pro Trp Thr Phe Gly Gly Gly Thr Lys
            115                 120                 125

Leu Glu Ile Lys
    130

<210> SEQ ID NO 45
<211> LENGTH: 411
<212> TYPE: DNA
<213> ORGANISM: Mus musculus

<400> SEQUENCE: 45
atgagagtgc tgattctttt gtgcctgttc acagcctttc ctggtatcct gtctgatgtg      60
cagcttcagg agtcaggacc tgacctggtg aaaccttctc agtcactttc actcacctgc     120
actgtcactg gctactccat caccagtggt tatagctggc actggatccg cagtttcca      180 ggaaacaaac tggaatggtt gggctacata cactatagtg gtagcactac ctacaaccca     240
tctctcaaag gtcggatctc tatcactcga gacacatcca agaaccagtt cttcctgcag     300
ttgaattctg tgactactga ggacactgcc acatattact gtgcaagatg gggtactggc     360
cactggtact cgatgtctg ggccgcaggg accacggtca ccgtctcctc a               411

<210> SEQ ID NO 46
<211> LENGTH: 137
<212> TYPE: PRT
<213> ORGANISM: Mus musculus

<400> SEQUENCE: 46

Met Arg Val Leu Ile Leu Leu Cys Leu Phe Thr Ala Phe Pro Gly Ile
1               5                   10                  15

Leu Ser Asp Val Gln Leu Gln Glu Ser Gly Pro Asp Leu Val Lys Pro
                20                  25                  30

Ser Gln Ser Leu Ser Leu Thr Cys Thr Val Thr Gly Tyr Ser Ile Thr
            35                  40                  45

Ser Gly Tyr Ser Trp His Trp Ile Arg Gln Phe Pro Gly Asn Lys Leu
        50                  55                  60

Glu Trp Leu Gly Tyr Ile His Tyr Ser Gly Ser Thr Thr Tyr Asn Pro
65                  70                  75                  80

Ser Leu Lys Gly Arg Ile Ser Ile Thr Arg Asp Thr Ser Lys Asn Gln
                85                  90                  95

Phe Phe Leu Gln Leu Asn Ser Val Thr Thr Glu Asp Thr Ala Thr Tyr

```
              100                 105                 110
Tyr Cys Ala Arg Trp Gly Thr Gly His Trp Tyr Phe Asp Val Trp Ala
            115                 120                 125
Ala Gly Thr Thr Val Thr Val Ser Ser
        130                 135

<210> SEQ ID NO 47
<211> LENGTH: 384
<212> TYPE: DNA
<213> ORGANISM: Mus musculus

<400> SEQUENCE: 47
atggcctgga tttcacttat actctctctc ctggctctca gctcagggc catttcccag      60 gctgttgtga ctcaggaatc tgcactcacc acatcacctg gtaaaacagt cacactcact    120
tgtcgctcaa gtactggggc tgttacaact actaactatg ccaactgggt ccaagaaaaa    180
ccagatcatt tattcactgg tctaataggt ggtaccaaca accgagttcc aggtgttcct    240
gccagattct caggctccct gattggagac aaggctgccc tcaccatcac aggggcacag    300
actgaggatg aggcaatata tttctgtgct ctatggtaca gcaaccattg ggtgttcggt    360
ggaggaacca aactgactgt ccta                                            384

<210> SEQ ID NO 48
<211> LENGTH: 128
<212> TYPE: PRT
<213> ORGANISM: Mus musculus

<400> SEQUENCE: 48

Met Ala Trp Ile Ser Leu Ile Leu Ser Leu Leu Ala Leu Ser Ser Gly
1               5                   10                  15

Ala Ile Ser Gln Ala Val Val Thr Gln Glu Ser Ala Leu Thr Thr Ser
            20                  25                  30

Pro Gly Lys Thr Val Thr Leu Thr Cys Arg Ser Ser Thr Gly Ala Val
        35                  40                  45

Thr Thr Thr Asn Tyr Ala Asn Trp Val Gln Glu Lys Pro Asp His Leu
    50                  55                  60

Phe Thr Gly Leu Ile Gly Gly Thr Asn Asn Arg Val Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
            100                 105                 110

Tyr Ser Asn His Trp Val Phe Gly Gly Gly Thr Lys Leu Thr Val Leu
        115                 120                 125
```